US012440328B2

(12) United States Patent
Pintor et al.

(10) Patent No.: US 12,440,328 B2
(45) Date of Patent: Oct. 14, 2025

(54) MODIFIED PROSTHETIC HEART VALVE STENT

(71) Applicant: Edwards Lifesciences Corporation, Irvine, CA (US)

(72) Inventors: Rafael Pintor, Mission Viejo, CA (US); Sai Prasad Uppalapati, Plano, TX (US)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 772 days.

(21) Appl. No.: 17/656,513

(22) Filed: Mar. 25, 2022

(65) Prior Publication Data

US 2022/0211492 A1 Jul. 7, 2022

Related U.S. Application Data

(63) Continuation of application No. PCT/US2020/052496, filed on Sep. 24, 2020.

(Continued)

(51) Int. Cl.
*A61F 2/24* (2006.01)

(52) U.S. Cl.
CPC .................................. *A61F 2/2418* (2013.01)

(58) Field of Classification Search
CPC ...... A61F 2/2418; A61F 2/2433; A61F 2/243; A61F 2/2409
See application file for complete search history.

(56) References Cited

U.S. PATENT DOCUMENTS

| | | | |
|---|---|---|---|
| 3,143,742 | A | 8/1964 | Cromie |
| 3,320,972 | A | 5/1967 | High et al. |

(Continued)

FOREIGN PATENT DOCUMENTS

| | | | |
|---|---|---|---|
| EP | 0125393 | B1 | 12/1987 |
| EP | 0143246 | B1 | 11/1991 |

(Continued)

OTHER PUBLICATIONS

Krakow, "3F Announces the First Clinical Implantation of the 3F Enable Aortic Heart Valve", Healthcare Sales&Marketing Network News Feed, Jan. 18, 2005, p. 1.

*Primary Examiner* — Melanie R Tyson
*Assistant Examiner* — Paris Marie Blass
(74) *Attorney, Agent, or Firm* — Guy Cumberbatch

(57) ABSTRACT

A prosthetic heart valve having an expandable stent modified to reduce the impact on the adjacent conduction system of the heart. A plurality of flexible leaflets arranged to close together along a flow axis through the valve prevent blood flow in one direction, and a support frame surrounds and supports the leaflets. The stent is defined by a plurality of connected struts arranged around a circumference. A pattern of the struts is consistent around the circumference except in a modified region on one side so that when converted to the expanded configuration the stent on the one side expands radially outward a smaller distance and/or has larger cells defined between the struts than around a remainder of the circumference. The stent may be connected to a non-collapsible valve member or the entire valve may be expandable. The valve may be for implant at the aortic annulus and the modified region may be centered at a commissure post of the support frame.

22 Claims, 14 Drawing Sheets

Related U.S. Application Data

(60) Provisional application No. 62/907,476, filed on Sep. 27, 2019.

(56) References Cited

U.S. PATENT DOCUMENTS

| | | | |
|---|---|---|---|
| 3,371,352 | A | 3/1968 | Siposs et al. |
| 3,409,013 | A | 11/1968 | Berry |
| 3,546,710 | A | 12/1970 | Ivanovich et al. |
| 3,574,865 | A | 4/1971 | Hamaker |
| 3,628,535 | A | 12/1971 | Ostrowsky et al. |
| 3,657,744 | A | 4/1972 | Ersek |
| 3,686,740 | A | 8/1972 | Shiley |
| 3,755,823 | A | 9/1973 | Hancock |
| 3,839,741 | A | 10/1974 | Haller |
| 3,997,923 | A | 12/1976 | Possis |
| 4,035,849 | A | 7/1977 | Angell et al. |
| 4,078,468 | A | 3/1978 | Civitello |
| 4,079,468 | A | 3/1978 | Liotta et al. |
| 4,084,268 | A | 4/1978 | Ionescu et al. |
| 4,106,129 | A | 8/1978 | Carpentier et al. |
| 4,172,295 | A | 10/1979 | Batten |
| 4,217,665 | A | 8/1980 | Bex et al. |
| 4,218,782 | A | 8/1980 | Rygg |
| 4,259,753 | A | 4/1981 | Liotta et al. |
| 4,340,091 | A | 7/1982 | Skelton et al. |
| 4,343,048 | A | 8/1982 | Ross et al. |
| 4,364,126 | A | 12/1982 | Rosen et al. |
| 4,388,735 | A | 6/1983 | Ionescu et al. |
| 4,441,216 | A | 4/1984 | Ionescu et al. |
| 4,451,936 | A | 6/1984 | Carpentier et al. |
| 4,470,157 | A | 9/1984 | Love |
| 4,490,859 | A | 1/1985 | Black et al. |
| 4,501,030 | A | 2/1985 | Lane |
| 4,506,394 | A | 3/1985 | Bedard |
| 4,535,483 | A | 8/1985 | Klawitter et al. |
| 4,605,407 | A | 8/1986 | Black et al. |
| 4,626,255 | A | 12/1986 | Reichart et al. |
| 4,629,459 | A | 12/1986 | Ionescu et al. |
| 4,680,031 | A | 7/1987 | Alonso |
| 4,687,483 | A | 8/1987 | Fisher et al. |
| 4,702,250 | A | 10/1987 | Ovil et al. |
| 4,705,516 | A | 11/1987 | Barone et al. |
| 4,725,274 | A | 2/1988 | Lane et al. |
| 4,731,074 | A | 3/1988 | Rousseau et al. |
| 4,778,461 | A | 10/1988 | Pietsch et al. |
| 4,790,843 | A | 12/1988 | Carpentier et al. |
| 4,851,000 | A | 7/1989 | Gupta |
| 4,865,600 | A | 9/1989 | Carpentier et al. |
| 4,888,009 | A | 12/1989 | Lederman et al. |
| 4,914,097 | A | 4/1990 | Oda et al. |
| 4,960,424 | A | 10/1990 | Grooters |
| 4,993,428 | A | 2/1991 | Arms |
| 5,010,892 | A | 4/1991 | Colvin et al. |
| 5,032,128 | A | 7/1991 | Alonso |
| 5,037,434 | A | 8/1991 | Lane |
| 5,147,391 | A | 9/1992 | Lane |
| 5,163,955 | A | 11/1992 | Love et al. |
| 5,258,023 | A | 11/1993 | Reger |
| 5,316,016 | A | 5/1994 | Adams et al. |
| 5,326,370 | A | 7/1994 | Love et al. |
| 5,326,371 | A | 7/1994 | Love et al. |
| 5,332,402 | A | 7/1994 | Teitelbaum |
| 5,360,444 | A | 11/1994 | Kusuhara |
| 5,370,685 | A | 12/1994 | Stevens |
| 5,376,112 | A | 12/1994 | Duran |
| 5,396,887 | A | 3/1995 | Imran |
| 5,397,351 | A | 3/1995 | Pavcnik et al. |
| 5,411,522 | A | 5/1995 | Trott |
| 5,423,887 | A | 6/1995 | Love et al. |
| 5,425,741 | A | 6/1995 | Lemp et al. |
| 5,431,676 | A | 7/1995 | Dubrul et al. |
| 5,449,384 | A | 9/1995 | Johnson |
| 5,449,385 | A | 9/1995 | Religa et al. |
| 5,469,868 | A | 11/1995 | Reger |
| 5,476,510 | A | 12/1995 | Eberhardt et al. |

| | | | |
|---|---|---|---|
| 5,488,789 | A | 2/1996 | Religa et al. |
| 5,489,297 | A | 2/1996 | Duran |
| 5,489,298 | A | 2/1996 | Love et al. |
| 5,500,016 | A | 3/1996 | Fisher |
| 5,533,515 | A | 7/1996 | Coller et al. |
| 5,549,665 | A | 8/1996 | Vesely et al. |
| 5,562,729 | A | 10/1996 | Purdy et al. |
| 5,571,215 | A | 11/1996 | Sterman et al. |
| 5,573,007 | A | 11/1996 | Bobo |
| 5,578,076 | A | 11/1996 | Krueger et al. |
| 5,584,803 | A | 12/1996 | Stevens et al. |
| 5,618,307 | A | 4/1997 | Donlon et al. |
| 5,626,607 | A | 5/1997 | Malecki et al. |
| 5,628,789 | A | 5/1997 | Vanney et al. |
| 5,693,090 | A | 12/1997 | Unsworth et al. |
| 5,695,503 | A | 12/1997 | Krueger et al. |
| 5,713,952 | A | 2/1998 | Vanney et al. |
| 5,716,370 | A | 2/1998 | Williamson et al. |
| 5,728,064 | A | 3/1998 | Burns et al. |
| 5,728,151 | A | 3/1998 | Garrison et al. |
| 5,735,894 | A | 4/1998 | Krueger et al. |
| 5,752,522 | A | 5/1998 | Murphy |
| 5,755,782 | A | 5/1998 | Love et al. |
| 5,766,240 | A | 6/1998 | Johnson |
| 5,776,187 | A | 7/1998 | Krueger et al. |
| 5,776,188 | A | 7/1998 | Shepherd et al. |
| 5,800,527 | A | 9/1998 | Jansen et al. |
| 5,814,097 | A | 9/1998 | Sterman et al. |
| 5,814,098 | A | 9/1998 | Hinnenkamp et al. |
| 5,824,064 | A | 10/1998 | Taheri |
| 5,824,068 | A | 10/1998 | Bugge |
| 5,840,081 | A | 11/1998 | Andersen et al. |
| 5,848,969 | A | 12/1998 | Panescu et al. |
| 5,855,563 | A | 1/1999 | Kaplan et al. |
| 5,855,601 | A | 1/1999 | Bessler et al. |
| 5,865,801 | A | 2/1999 | Houser |
| 5,891,160 | A | 4/1999 | Williamson et al. |
| 5,895,420 | A | 4/1999 | Mirsch et al. |
| 5,902,308 | A | 5/1999 | Murphy |
| 5,908,450 | A | 6/1999 | Gross et al. |
| 5,919,147 | A | 7/1999 | Jain |
| 5,921,934 | A | 7/1999 | Teo |
| 5,921,935 | A | 7/1999 | Hickey |
| 5,924,984 | A | 7/1999 | Rao |
| 5,928,281 | A | 7/1999 | Huynh et al. |
| 5,957,949 | A | 9/1999 | Leonhardt et al. |
| 5,972,004 | A | 10/1999 | Williamson et al. |
| 5,984,959 | A | 11/1999 | Robertson et al. |
| 5,984,973 | A | 11/1999 | Girard et al. |
| 6,010,531 | A | 1/2000 | Donlon et al. |
| 6,042,607 | A | 3/2000 | Williamson et al. |
| 6,059,827 | A | 5/2000 | Fenton |
| 6,066,160 | A | 5/2000 | Colvin et al. |
| 6,074,418 | A | 6/2000 | Buchanan et al. |
| 6,081,737 | A | 6/2000 | Shah |
| 6,083,179 | A | 7/2000 | Oredsson |
| 6,099,475 | A | 8/2000 | Seward et al. |
| 6,106,550 | A | 8/2000 | Magovern et al. |
| 6,110,200 | A | 8/2000 | Hinnenkamp |
| 6,117,091 | A | 9/2000 | Young et al. |
| 6,126,007 | A | 10/2000 | Kari et al. |
| 6,264,611 | B1 | 7/2001 | Ishikawa et al. |
| 6,322,526 | B1 | 11/2001 | Rosenman et al. |
| 6,350,282 | B1 | 2/2002 | Eberhardt |
| 6,491,624 | B1 | 12/2002 | Lotfi |
| 6,773,457 | B2 | 8/2004 | Ivancev et al. |
| 7,037,333 | B2 | 5/2006 | Myers et al. |
| 7,998,151 | B2 | 8/2011 | St. Goar et al. |
| 8,308,798 | B2 | 11/2012 | Pintor et al. |
| 8,323,337 | B2 | 12/2012 | Gurskis et al. |
| 8,348,998 | B2 | 1/2013 | Pintor et al. |
| 8,641,757 | B2 | 2/2014 | Pintor et al. |
| 9,522,062 | B2 * | 12/2016 | Tuval .................... A61F 2/2409 |
| 2001/0021872 | A1 | 9/2001 | Bailey et al. |
| 2001/0039435 | A1 | 11/2001 | Roue et al. |
| 2001/0039436 | A1 | 11/2001 | Frazier et al. |
| 2001/0041914 | A1 | 11/2001 | Frazier et al. |
| 2001/0041915 | A1 | 11/2001 | Roue et al. |
| 2001/0049492 | A1 | 12/2001 | Frazier et al. |

(56) References Cited

U.S. PATENT DOCUMENTS

| | | | |
|---|---|---|---|
| 2002/0026238 | A1 | 2/2002 | Lane et al. |
| 2002/0032481 | A1 | 3/2002 | Gabbay |
| 2002/0058995 | A1 | 5/2002 | Stevens |
| 2002/0123802 | A1 | 9/2002 | Snyders |
| 2002/0138138 | A1 | 9/2002 | Yang |
| 2002/0151970 | A1 | 10/2002 | Garrison et al. |
| 2002/0188348 | A1 | 12/2002 | DiMatteo et al. |
| 2002/0198594 | A1 | 12/2002 | Schreck |
| 2003/0014104 | A1 | 1/2003 | Cribier |
| 2003/0023300 | A1 | 1/2003 | Bailey et al. |
| 2003/0023303 | A1 | 1/2003 | Palmaz et al. |
| 2003/0036795 | A1 | 2/2003 | Andersen et al. |
| 2003/0040792 | A1 | 2/2003 | Gabbay |
| 2003/0055495 | A1 | 3/2003 | Pease et al. |
| 2003/0105519 | A1 | 6/2003 | Fasol et al. |
| 2003/0109924 | A1 | 6/2003 | Cribier |
| 2003/0114913 | A1 | 6/2003 | Spenser et al. |
| 2003/0130729 | A1 | 7/2003 | Paniagua et al. |
| 2003/0149478 | A1 | 8/2003 | Figulla et al. |
| 2003/0167089 | A1 | 9/2003 | Lane |
| 2003/0236568 | A1 | 12/2003 | Hojeibane et al. |
| 2004/0019374 | A1 | 1/2004 | Hojeibane et al. |
| 2004/0034411 | A1 | 2/2004 | Quijano et al. |
| 2004/0044406 | A1 | 3/2004 | Woolfson et al. |
| 2004/0106976 | A1 | 6/2004 | Bailey et al. |
| 2004/0122514 | A1 | 6/2004 | Fogarty et al. |
| 2004/0122516 | A1 | 6/2004 | Fogarty et al. |
| 2004/0167573 | A1 | 8/2004 | Williamson et al. |
| 2004/0186563 | A1 | 9/2004 | Lobbi |
| 2004/0186565 | A1 | 9/2004 | Schreck |
| 2004/0193261 | A1 | 9/2004 | Berreklouw |
| 2004/0206363 | A1 | 10/2004 | McCarthy et al. |
| 2004/0210304 | A1 | 10/2004 | Seguin et al. |
| 2004/0210305 | A1 | 10/2004 | Shu et al. |
| 2004/0210307 | A1 | 10/2004 | Khairkhahan |
| 2004/0225355 | A1 | 11/2004 | Stevens |
| 2004/0236411 | A1 | 11/2004 | Sarac et al. |
| 2004/0260389 | A1 | 12/2004 | Case et al. |
| 2004/0260390 | A1 | 12/2004 | Sarac et al. |
| 2005/0010285 | A1 | 1/2005 | Lambrecht et al. |
| 2005/0027348 | A1 | 2/2005 | Case et al. |
| 2005/0033398 | A1 | 2/2005 | Seguin |
| 2005/0043760 | A1 | 2/2005 | Fogarty et al. |
| 2005/0043790 | A1 | 2/2005 | Seguin |
| 2005/0060029 | A1 | 3/2005 | Le et al. |
| 2005/0065594 | A1 | 3/2005 | DiMatteo et al. |
| 2005/0065614 | A1 | 3/2005 | Stinson |
| 2005/0075584 | A1 | 4/2005 | Cali |
| 2005/0075713 | A1 | 4/2005 | Biancucci et al. |
| 2005/0075717 | A1 | 4/2005 | Nguyen et al. |
| 2005/0075718 | A1 | 4/2005 | Nguyen et al. |
| 2005/0075719 | A1 | 4/2005 | Bergheim |
| 2005/0075720 | A1 | 4/2005 | Nguyen et al. |
| 2005/0075724 | A1 | 4/2005 | Svanidze et al. |
| 2005/0080454 | A1 | 4/2005 | Drews et al. |
| 2005/0096738 | A1 | 5/2005 | Cali et al. |
| 2005/0137682 | A1 | 6/2005 | Justino |
| 2005/0137686 | A1 | 6/2005 | Salahieh et al. |
| 2005/0137687 | A1 | 6/2005 | Salahieh et al. |
| 2005/0137688 | A1 | 6/2005 | Salahieh et al. |
| 2005/0137689 | A1 | 6/2005 | Salahieh et al. |
| 2005/0137690 | A1 | 6/2005 | Salahieh et al. |
| 2005/0137691 | A1 | 6/2005 | Salahieh et al. |
| 2005/0137692 | A1 | 6/2005 | Haug et al. |
| 2005/0137694 | A1 | 6/2005 | Haug et al. |
| 2005/0137695 | A1 | 6/2005 | Salahieh et al. |
| 2005/0137702 | A1 | 6/2005 | Haug et al. |
| 2005/0159811 | A1 | 7/2005 | Lane |
| 2005/0165477 | A1 | 7/2005 | Anduiza et al. |
| 2005/0165479 | A1 | 7/2005 | Drews et al. |
| 2005/0182483 | A1 | 8/2005 | Osborne et al. |
| 2005/0182486 | A1 | 8/2005 | Gabbay |
| 2005/0192665 | A1 | 9/2005 | Spenser et al. |
| 2005/0203616 | A1 | 9/2005 | Cribier |
| 2005/0203617 | A1 | 9/2005 | Forster et al. |
| 2005/0203618 | A1 | 9/2005 | Sharkawy et al. |
| 2005/0216079 | A1 | 9/2005 | MaCoviak |
| 2005/0222674 | A1 | 10/2005 | Paine |
| 2005/0234546 | A1 | 10/2005 | Nugent et al. |
| 2005/0240259 | A1 | 10/2005 | Sisken et al. |
| 2005/0251252 | A1 | 11/2005 | Stobie |
| 2005/0261765 | A1 | 11/2005 | Liddicoat |
| 2005/0283231 | A1 | 12/2005 | Haug et al. |
| 2006/0025857 | A1 | 2/2006 | Bergheim et al. |
| 2006/0052867 | A1 | 3/2006 | Revuelta et al. |
| 2006/0058871 | A1 | 3/2006 | Zakay et al. |
| 2006/0058872 | A1 | 3/2006 | Salahieh et al. |
| 2006/0074484 | A1 | 4/2006 | Huber |
| 2006/0085060 | A1 | 4/2006 | Campbell |
| 2006/0095125 | A1 | 5/2006 | Chinn et al. |
| 2006/0122634 | A1 | 6/2006 | Ino et al. |
| 2006/0122692 | A1 | 6/2006 | Gilad et al. |
| 2006/0136054 | A1 | 6/2006 | Berg et al. |
| 2006/0149360 | A1 | 7/2006 | Schwammenthal et al. |
| 2006/0154230 | A1 | 7/2006 | Cunanan et al. |
| 2006/0161249 | A1 | 7/2006 | Realyvasquez et al. |
| 2006/0167543 | A1 | 7/2006 | Bailey et al. |
| 2006/0195183 | A1 | 8/2006 | Navia et al. |
| 2006/0195184 | A1 | 8/2006 | Lane et al. |
| 2006/0195185 | A1 | 8/2006 | Lane et al. |
| 2006/0195186 | A1 | 8/2006 | Drews et al. |
| 2006/0207031 | A1 | 9/2006 | Cunanan et al. |
| 2006/0229708 | A1 | 10/2006 | Powell et al. |
| 2006/0235508 | A1 | 10/2006 | Lane et al. |
| 2006/0241745 | A1 | 10/2006 | Solem |
| 2006/0246888 | A1 | 11/2006 | Bender et al. |
| 2006/0253191 | A1 | 11/2006 | Salahieh et al. |
| 2006/0259134 | A1 | 11/2006 | Schwammenthal et al. |
| 2006/0259135 | A1 | 11/2006 | Navia et al. |
| 2006/0259136 | A1 | 11/2006 | Nguyen et al. |
| 2006/0265056 | A1 | 11/2006 | Nguyen et al. |
| 2006/0271172 | A1 | 11/2006 | Tehrani |
| 2006/0271175 | A1 | 11/2006 | Woolfson et al. |
| 2006/0287717 | A1 | 12/2006 | Rowe et al. |
| 2006/0287719 | A1 | 12/2006 | Rowe et al. |
| 2006/0293745 | A1 | 12/2006 | Carpentier et al. |
| 2007/0005129 | A1 | 1/2007 | Damm et al. |
| 2007/0010876 | A1 | 1/2007 | Salahieh et al. |
| 2007/0010877 | A1 | 1/2007 | Salahieh et al. |
| 2007/0016285 | A1 | 1/2007 | Lane et al. |
| 2007/0016286 | A1 | 1/2007 | Herrmann et al. |
| 2007/0016288 | A1 | 1/2007 | Gurskis et al. |
| 2007/0043435 | A1 | 2/2007 | Seguin et al. |
| 2007/0078509 | A1 | 4/2007 | Lotfy |
| 2007/0078510 | A1 | 4/2007 | Ryan |
| 2007/0100440 | A1 | 5/2007 | Figulla et al. |
| 2007/0129794 | A1 | 6/2007 | Realyvasquez |
| 2007/0142906 | A1 | 6/2007 | Figulla et al. |
| 2007/0142907 | A1 | 6/2007 | Moaddeb et al. |
| 2007/0150053 | A1 | 6/2007 | Gurskis et al. |
| 2007/0156233 | A1 | 7/2007 | Kapadia et al. |
| 2007/0162103 | A1 | 7/2007 | Case et al. |
| 2007/0162107 | A1 | 7/2007 | Haug et al. |
| 2007/0162111 | A1 | 7/2007 | Fukamachi et al. |
| 2007/0179604 | A1 | 8/2007 | Lane |
| 2007/0185565 | A1 | 8/2007 | Schwammenthal et al. |
| 2007/0198097 | A1 | 8/2007 | Zegdi |
| 2007/0203575 | A1 | 8/2007 | Forster et al. |
| 2007/0203576 | A1 | 8/2007 | Lee et al. |
| 2007/0213813 | A1 | 9/2007 | Von Segesser et al. |
| 2007/0225801 | A1 | 9/2007 | Drews et al. |
| 2007/0233237 | A1 | 10/2007 | Krivoruchko |
| 2007/0239266 | A1 | 10/2007 | Birdsall |
| 2007/0239269 | A1 | 10/2007 | Dolan et al. |
| 2007/0239273 | A1 | 10/2007 | Allen |
| 2007/0244546 | A1 | 10/2007 | Francis |
| 2007/0244558 | A1 | 10/2007 | Machiraju |
| 2007/0255398 | A1 | 11/2007 | Yang et al. |
| 2007/0260305 | A1 | 11/2007 | Drews et al. |
| 2007/0265701 | A1 | 11/2007 | Gurskis et al. |
| 2007/0270944 | A1 | 11/2007 | Bergheim et al. |
| 2007/0282436 | A1 | 12/2007 | Pinchuk |
| 2007/0288089 | A1 | 12/2007 | Gurskis et al. |
| 2008/0021546 | A1 | 1/2008 | Patz et al. |

(56) References Cited

U.S. PATENT DOCUMENTS

2008/0033543 A1 2/2008 Gurskis et al.
2008/0065198 A1 3/2008 Quintessenza
2008/0119875 A1 5/2008 Ino et al.
2008/0154355 A1* 6/2008 Benichou .............. A61F 2/2418 623/1.26
2008/0154356 A1 6/2008 Obermiller et al.
2008/0281411 A1 11/2008 Berreklouw
2008/0319543 A1 12/2008 Lane
2009/0036903 A1 2/2009 Ino et al.
2009/0192599 A1 7/2009 Lane et al.
2009/0192602 A1 7/2009 Kuehn
2009/0192603 A1 7/2009 Ryan
2009/0192604 A1 7/2009 Gloss
2009/0192605 A1 7/2009 Gloss et al.
2009/0192606 A1 7/2009 Gloss et al.
2010/0161036 A1 6/2010 Pintor et al.
2010/0249894 A1 9/2010 Oba et al.
2010/0249908 A1* 9/2010 Chau ..................... A61F 2/2418 623/1.26
2010/0331972 A1 12/2010 Pintor et al.
2011/0022165 A1 1/2011 Oba et al.
2011/0040372 A1 2/2011 Hansen et al.
2011/0147251 A1 6/2011 Hodshon et al.
2011/0218619 A1* 9/2011 Benichou .............. A61F 2/2418 623/2.11
2012/0065729 A1* 3/2012 Pintor ................... A61F 2/2418 623/2.14
2012/0123529 A1* 5/2012 Levi ...................... A61F 2/2433 623/2.11
2012/0141656 A1 6/2012 Orr et al.
2012/0150288 A1 6/2012 Hodshon et al.
2013/0046373 A1* 2/2013 Cartledge ............... A61F 2/966 623/1.11
2013/0053949 A1 2/2013 Pintor et al.
2013/0116777 A1 5/2013 Pintor et al.
2014/0058194 A1 2/2014 Soletti et al.
2014/0079758 A1 3/2014 Hall et al.
2014/0277412 A1* 9/2014 Bortlein ................ A61F 2/2418 623/2.11
2016/0000559 A1* 1/2016 Chen ..................... A61F 2/2412 623/2.15
2016/0120643 A1* 5/2016 Kupumbati ........... A61F 2/2436 623/2.11
2016/0278922 A1* 9/2016 Braido ...................... A61F 2/89
2017/0360558 A1* 12/2017 Ma ........................ A61F 2/2418
2018/0153690 A1* 6/2018 Spence ................. A61F 2/2418

FOREIGN PATENT DOCUMENTS

EP 2531115 A2 12/2012
KR 1020090024249 A 3/2009
SU 1116573 A 7/1985
SU 1697790 A1 12/1991
WO 1992013502 A1 8/1992
WO 1997042871 A1 11/1997
WO 2007146261 A2 12/2007
WO WO-2013075215 A1 * 5/2013 ........... A61F 2/2403
WO WO-2017196912 A1 11/2017

* cited by examiner

Electrical system of the heart

MODIFIED PROSTHETIC HEART VALVE STENT

CROSS REFERENCE TO RELATED APPLICATIONS

This application is a continuation of International Patent Application No. PCT/US2020/052496, filed Sep. 24, 2020, which claims the benefit of U.S. Patent Application No. 62/907,476, filed Sep. 27, 2019, the entire disclosures all of which are incorporated by reference for all purposes.

TECHNICAL FIELD

The present disclosure generally relates to controlled expansion of a prosthetic heart valve stent and, more particularly, to modifications and/or asymmetric expansion of a subvalvular stent to avoid compression and potential mechanical injury to the heart's electrical conduction system.

BACKGROUND

Heart valve disease continues to be a significant cause of morbidity and mortality, resulting from a number of ailments including rheumatic fever and birth defects. Currently, the primary treatment of aortic valve disease is valve replacement. Worldwide, an estimated 300,000 heart valve replacement surgeries are performed annually. Many patients receive bioprosthetic heart valve replacements, which utilize biologically derived tissues for flexible fluid occluding leaflets. The most successful bioprosthetic materials for flexible leaflets are whole porcine valves and separate leaflets made from bovine pericardium stitched together to form a tri-leaflet valve. The most common flexible leaflet valve construction includes three leaflets mounted to commissure posts around a peripheral non-expandable support structure with free edges that project toward an outflow direction and meet or coapt in the middle of the flowstream. A suture-permeable sewing ring is provided around the inflow end.

In recent years, advancements in minimally-invasive surgery and interventional cardiology have encouraged some investigators to pursue percutaneous repair and/or replacement of heart valves. One prosthetic valve for use in such a procedure can include a radially collapsible and expandable frame to which leaflets of the prosthetic valve can be coupled. For example, U.S. Pat. Nos. 6,730,118, 7,393,360, 7,510,575, and 7,993,394, which are incorporated herein by reference, describe exemplary collapsible transcatheter heart valves (THVs). Edwards Lifesciences of Irvine, Calif., has developed a plastically- or balloon-expandable stent integrated with a bioprosthetic valve. The stent/valve device, now called the Edwards Sapien® Heart Valve, is deployed across the native diseased valve to permanently hold the valve open, thereby alleviating a need to excise the native valve.

Another prior bioprosthetic valve for aortic valve replacement is provided by the Edwards Intuity Elite® valve system also available from Edwards Lifesciences. Aspects of the system are disclosed in U.S. Pat. Nos. 8,641,757 and 9,370,418 both to Pintor, et al. and 8,869,982 to Hodshon, et al. The Edwards Intuity Elite® valve is a hybrid of a generally non-expandable valve member and an expandable anchoring stent that helps secure the valve in place in a shorter amount of time. The implant process only requires three sutures which reduces the time-consuming process of tying knots. A delivery system advances the Edwards Intuity valve with the stent at the leading end until it is located within the left ventricular outflow tract (LVOT), at which point a balloon inflates to expand the stent against the left ventricular outflow tract wall.

With all expandable prosthetic heart valves, there is the potential that under certain conditions the expanding stent could impinge on the conduction system of the heart, therefore affecting its function. Solutions are needed.

SUMMARY

The present application provides a prosthetic heart valve comprising a plurality of flexible leaflets arranged to close together along a flow axis through the valve to prevent blood flow in one direction, and a support frame surrounding and supporting the leaflets. An expandable stent connected to the support frame defines a circumference and is convertible from a radially contracted configuration to a radially expanded configuration. The stent is defined by a plurality of interconnected struts, wherein a pattern of the interconnected struts is consistent around the circumference except in a modified region on one circumferential side so that when converted to the expanded configuration the modified region of the stent expands radially outward a smaller distance than around a remainder of the circumference. Alternatively, the modified region when converted to the expanded configuration has larger cells defined between the interconnected struts than around a remainder of the circumference The support frame may be non-expandable, non-collapsible and the expandable stent connects to an inflow end of the support frame and is generally non-expandable and non-collapsible as a consequence, and wherein the expandable stent has an inflow end that converts from the radially contracted configuration to the radially expanded configuration. Preferably, the expandable stent is plastically-expandable.

The plurality of interconnected struts may include a series of circumferential rows of row struts between axial columns of column struts, the row struts defining bends between the column struts, and wherein at least one row strut in the modified region in at least one row defines shallower bends than outside of the modified region. The final bend angles of the at least one row strut in the modified region are preferably between about 135-160°, while final bend angles around the remainder of the at least one row strut are preferably between about 45-90°.

The heart valve may be configured for implant at an aortic annulus and defines three commissure posts at intersections between three of the flexible leaflets, and the modified region is centered at one of the three commissure posts and will correspond to the location of the membranous interventricular septum and the conduction system zone. Desirably, the modified region extends circumferentially between about 90-120°.

In one embodiment, the support frame is expandable and the expandable stent forms a portion of the support frame such that the heart valve is fully expandable. The support frame in the fully expandable heart valve may be plastically-expandable or self-expandable.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained, and other advantages and features will appear with reference to the accompanying schematic drawings wherein.

DETAILED DESCRIPTION OF CERTAIN EMBODIMENTS

As mentioned above, one promising prior art technique for heart valve replacement is a hybrid valve with a non-expandable valve member and an expandable stent thereon which, though still requiring cardiopulmonary bypass, can be implanted in a much shorter time frame. The hybrid valve is delivered through direct-access ports introduced through the chest.

Hybrid Heart Valve

Figure 1:
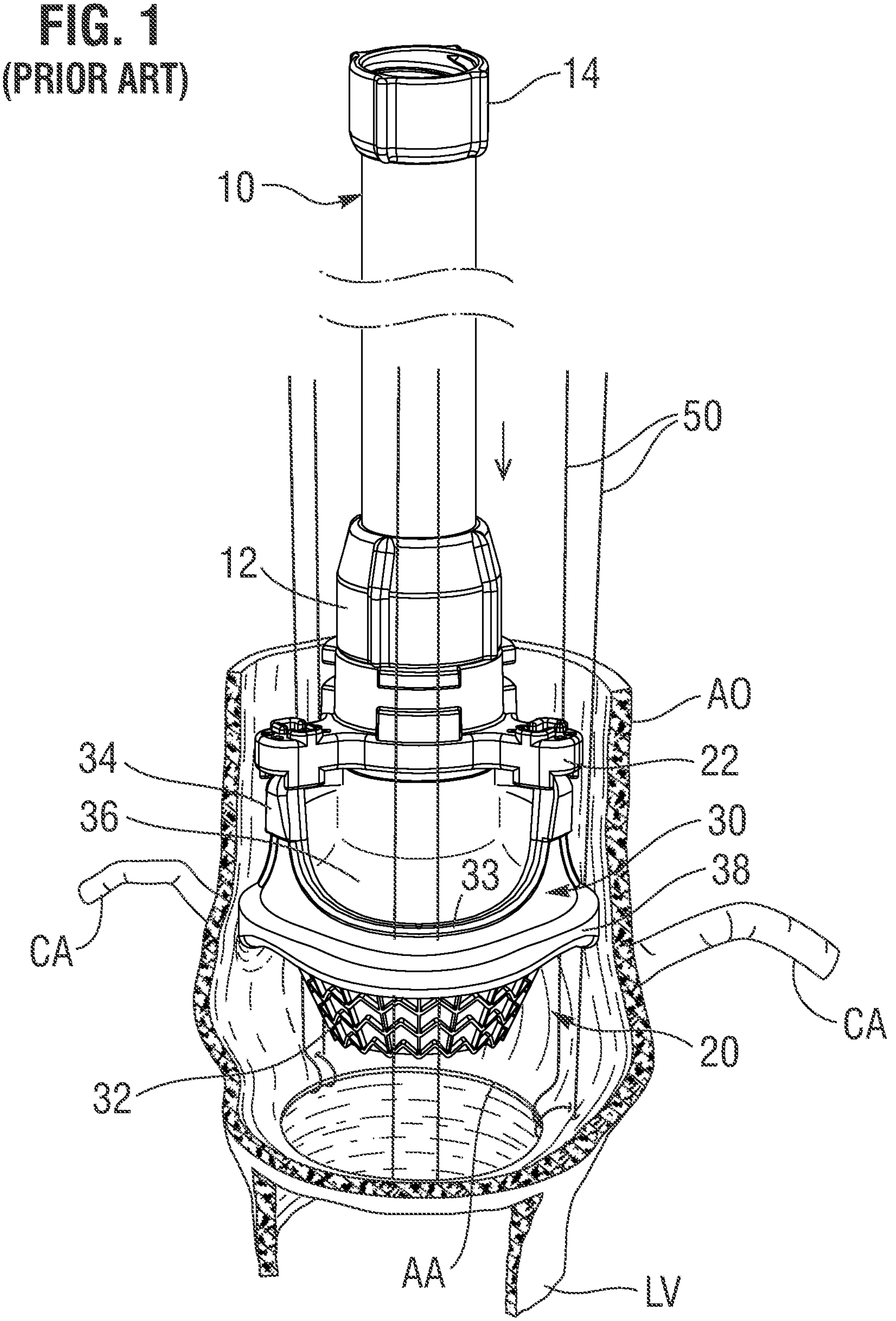
FIG. 1 (PRIOR ART)
FIG. 1 illustrates delivery to an aortic annulus of a prior art heart valve/holder combination using a valve delivery tube.

FIG. 1 illustrates a snapshot in the process of delivering a prior art heart valve 20 to an aortic annulus AA using a valve delivery tube or handle 10. As will be seen, the valve delivery handle 10 has a distal coupler 12 and a proximal coupler 14. For purpose of orientation, the heart valve 20 has an inflow end down and an outflow end up, and the terms proximal and distal are defined from the perspective of the surgeon delivering the valve inflow end first. Thus, proximal is synonymous with up or outflow, and distal with down or inflow.

Figure 2:
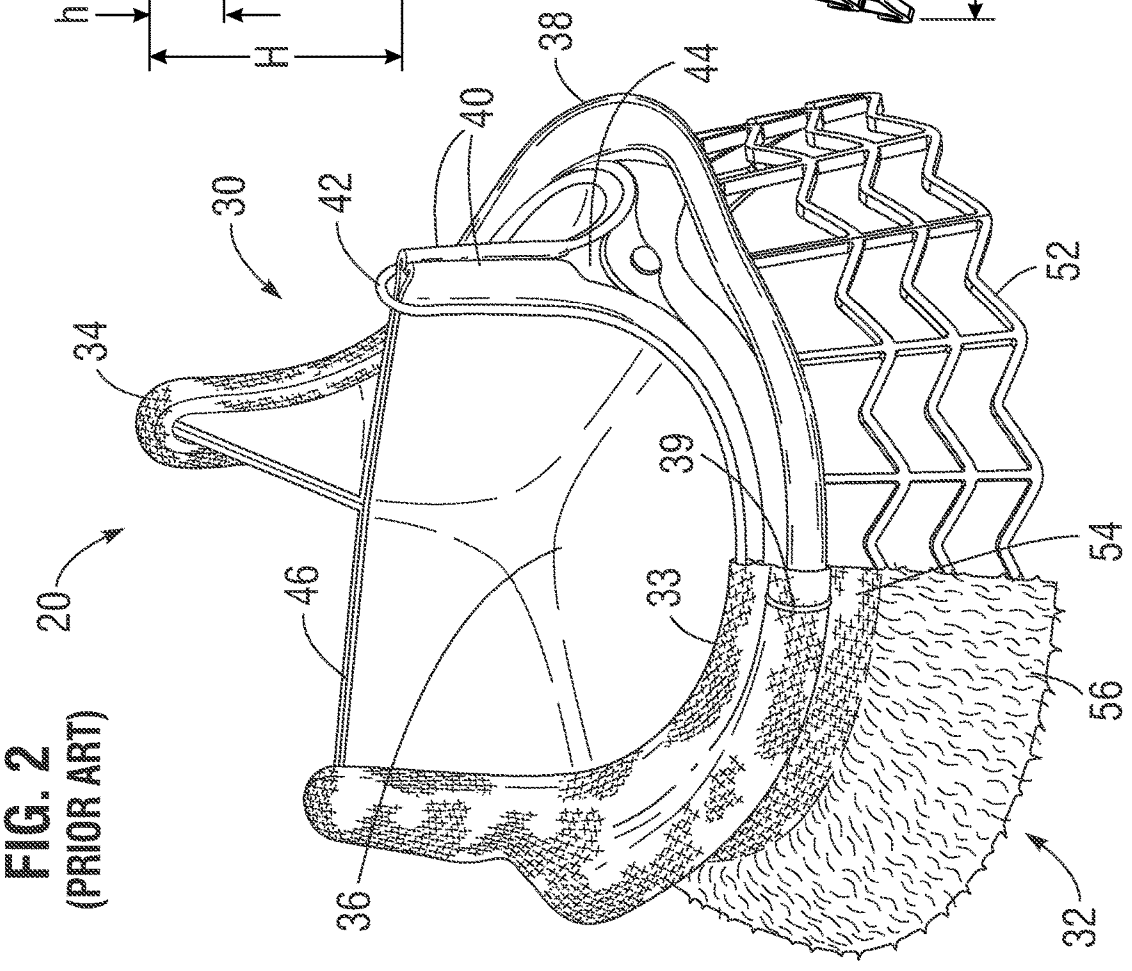
FIG. 2 (PRIOR ART)
FIG. 2 is a partially cutaway perspective view of a prior art assembled hybrid prosthetic heart valve.

As also illustrated in FIG. 2, the prosthetic heart valve 20 is considered a hybrid type because it has a non-expandable, non-collapsible valve member 30 and an expandable anchoring skirt 32 attached to and projecting from a distal end of the valve member 30. The valve member 30 can take a variety of forms, and may include a cloth-covered wireform that follows an undulating path around the periphery of the valve with alternating cusps 33 and commissure posts 34. A plurality of flexible leaflets 36 extend across a generally circular orifice defined within the valve member 30, each of which receives peripheral support along the wireform, in particular by two adjacent commissure posts 34. An annular, preferably contoured, sewing or sealing ring 38 circumscribes the valve 20 at an axial location approximately between the valve member 30 and expandable anchoring skirt 32. Three markings 39 are often evenly spaced around the cloth-covered sealing ring 38 to delineate to the surgeon the center of each of the cusps 33.

The term "valve member" refers to that component of a heart valve that possesses the fluid occluding surfaces to prevent blood flow in one direction while permitting it in another. Various constructions of valve members are available. The leaflets may be bioprosthetic, synthetic, or other suitable expedients. When used for aortic valve replacement, the valve member 30 preferably has three flexible leaflets 36 which provide the fluid occluding surfaces to replace the function of the native valve leaflets. In various preferred embodiments, the valve leaflets may be taken from another human heart (cadaver), a cow (bovine), a pig (porcine valve) or a horse (equine). The three leaflets are supported by an internal generally tubular frame, which typically include a synthetic (metallic and/or polymeric) support structure of one or more components covered with cloth for ease of attachment of the leaflets.

Although the exemplary heart valve 20 is constructed as mentioned, the present invention is broader and encompasses any valve member 30 having an expandable anchoring skirt 32 projecting from an inflow end thereof (for example, one without a wireform).

For definitional purposes, the terms "skirt" or "anchoring skirt" refer to an expandable structural component of a heart valve that is capable of attaching to tissue of a heart valve annulus. The anchoring skirt 32 described herein may be tubular or conical, and have varying shapes or diameters.

By utilizing an expandable skirt 32 coupled to a non-expandable valve member 30, the duration of the implant operation is greatly reduced as compared with a conventional sewing procedure utilizing an array of sutures. The expandable skirt 32 may simply be radially expanded outward into contact with the implantation site, or may be provided with additional anchoring means, such as barbs. This provides a rapid connection means as it does not require the time-consuming process of suturing the valve entirely around the annulus. The operation may be carried out using a conventional open-heart approach and cardiopulmonary bypass. In one advantageous feature, the time on bypass is greatly reduced due to the relative speed of implanting the expandable stent.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause such as fluid dynamics acting on leaflets or commissures. Conversely, "non-expandable" should not be interpreted to mean completely rigid or dimensionally stable, merely that the valve member is not expandable/collapsible like some proposed minimally-invasively or percutaneously-delivered valves, and some slight expansion of conventional "non-expandable" heart valves, for example, may be observed.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a mitral valve replacement will be implanted at the mitral annulus. Certain features of the present invention are particularly advantageous for one implantation site or the other, in particular the aortic annulus. However, unless the combination is structurally impossible, or excluded by claim language, any of the heart valve embodiments described herein could be implanted in any body channel.

In a particularly preferred embodiment, the prosthetic valve 20 comprises a commercially available, non-expandable prosthetic valve member 30, such as the Carpentier-Edwards PERIMOUNT Magna® Aortic Heart Valve available from Edwards Lifesciences, while the anchoring skirt 32 includes an inner plastically-expandable stent frame covered with fabric. In another embodiment, the valve member 30 comprises a PERIMOUNT Magna® Aortic valve subjected to Resilia® tissue treatment, which allows for dry packaging and sterilization and eliminates the need to rinse the valves before implantation. In this sense, a "commercially available" prosthetic heart valve is an off-the-shelf (e.g., suitable for stand-alone sale and use) prosthetic heart valve defining therein a non-expandable, non-collapsible support structure and having a sealing ring capable of being implanted using sutures through the sealing ring in an open-heart, surgical procedure.

In the cutaway portion of FIG. 2, each of the three leaflets 36 includes outwardly projecting tabs 40 that pass through inverted U-shaped commissure posts 42 of an undulating wireform and wrap around cloth-covered upstanding posts 44 of an inner polymer band. Tabs 40 from adjacent leaflets converge outside of the wireform commissure posts 42 and are sewn together to provide an outer anchor for the leaflet free edges 46. In use, fluid forces close the leaflets (coaptation) as seen in FIG. 2 and exert substantial force on the occluded valve, which translates into inward force on the leaflet free edges 46. The assembly of the wrapped leaflet tabs 40 and cloth-covered posts 44 sewn together provides a solid anchor that is prevented from inward movement by the metallic wireform posts 42. Some flexing is acceptable and even desirable.

One feature of the valve member 30 that is often utilized is the sewing or sealing ring 38 that surrounds the inflow end thereof. The sealing ring 38 conforms to an upper end of the anchoring skirt 32 and is located at the junction of the skirt and the valve member 30. Moreover, the sealing ring 38 presents an outward flange that contacts an outflow side of the part of annulus, while the anchoring skirt 32 expands and contacts the opposite, ventricular side of the annulus, therefore securing the heart valve 20 to the annulus from both sides. Furthermore, the presence of the sealing ring 38 provides an opportunity for the surgeon to use conventional sutures to secure the heart valve 20 to the annulus as a contingency.

The preferred sealing ring 38 defines an undulating upper or outflow face and an undulating lower face. Cusps 33 of the valve structure abut valleys in the sealing ring 38 upper face opposite locations where the lower face defines peaks. Conversely, the valve commissure posts 34 align with locations where the sealing ring 38 lower face defines valleys or troughs. The undulating shape of the sealing ring 38 advantageously matches the anatomical contours of the aortic side of the annulus AA, that is, the supra-annular shelf. The ring 38 preferably comprises a suture-permeable material such as rolled synthetic fabric or a silicone inner core covered by a synthetic fabric. In the latter case, the silicone may be molded to define the undulating contour and the fabric cover conforms thereover.

As seen in FIG. 2, the anchoring skirt 32 comprises an inner stent frame 52 assembled within a tubular section of fabric 54 which is then drawn taut around the stent frame, inside and out, and sewn thereto to form the cloth-covered skirt 32. A thicker, more plush fabric flange 56 may also be attached around the fabric 54 for additional paravalvular sealing benefits. It should be noted that FIG. 2 shows the stent frame 52 in an outwardly expanded state, which occurs during and after implant as mentioned.

Figure 2A:
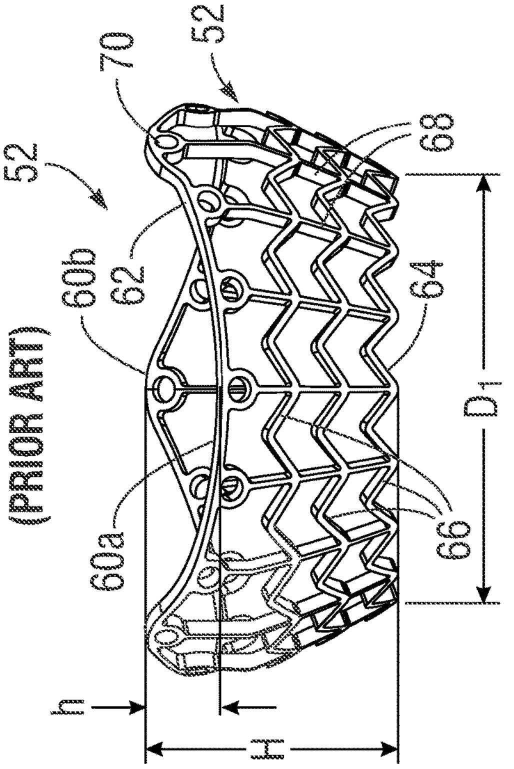
FIG. 2A (PRIOR ART)
FIGS. 2A and 2B are elevational views of a prior art anchoring skirt used in the hybrid prosthetic heart valve and shown in both radially contracted and expanded states, respectively.
Figure 2B:
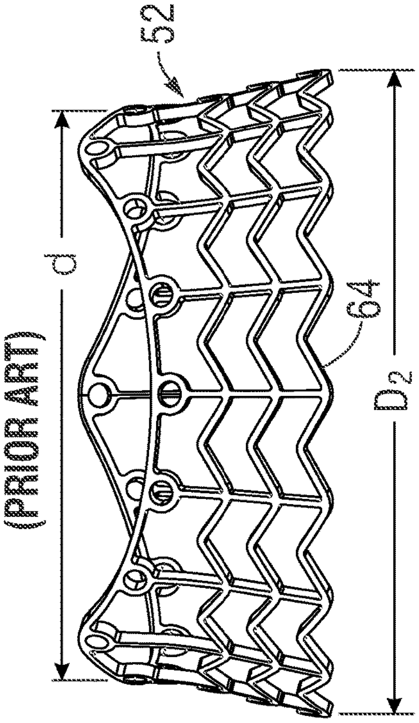
FIG. 2B (PRIOR ART)

In an assembly process, the stent frame 52 may be initially tubular and then crimped to a conical shape as see in FIG. 2A, for example. Of course, the frame 52 may be crimped first and then covered with cloth, or vice versa. FIG. 2B shows the expanded stent frame 52 isolated and expanded into its implant shape, which is generally conical and slightly flared out at a lower end.

With reference again to the implant step of FIG. 1, the aortic annulus AA is shown schematically isolated and it should be understood that various anatomical structures are not shown for clarity. The annulus AA includes a fibrous ring of tissue that projects inward from surrounding heart walls. The annulus AA defines an orifice between the ascending aorta AO and the left ventricle LV. Although not shown, native leaflets project inward at the annulus AA to form a one-way valve at the orifice. The leaflets are preferably left in place and outwardly compressed by the expandable anchoring skirt 32, or in some cases may be removed prior to the procedure. If the leaflets are removed, some of the calcified annulus may also be removed, such as with a rongeur. The ascending aorta AO commences at the annulus AA with three outward bulges or sinuses, two of which are centered at coronary ostia (openings) leading to coronary arteries CA. It is important to orient the prosthetic valve 20 so that the commissure posts 34 are not aligned with and thus not blocking the coronary ostia.

FIG. 1 shows a plurality of pre-installed guide sutures 50. The surgeon attaches the guide sutures 50 at three evenly spaced locations around the aortic annulus AA. In the illustrated embodiment, the guide sutures 50 attach to locations below or corresponding to the nadirs of the native cusps or sinuses. The guide sutures 50 are passed through the annulus AA and back out of the implantation site. Of course, other suturing methods or pledgets may be used depending on surgeon preference.

The guide sutures 50 extend in pairs of free lengths from the annulus AA and out of the operating site. The prosthetic heart valve 20 mounts on the distal end of the delivery handle 10 and the surgeon advances the valve into position within the aortic annulus AA along the guide sutures 50. That is, the surgeon threads the three pairs of guide sutures 50 through evenly spaced locations around the suture-permeable ring 38. If the guide sutures 50, as illustrated, anchor to the annulus AA below the aortic sinuses, they thread through the ring 38 mid-way between the valve commissure posts 34, in particular at cusp regions 33 of the sealing ring that may be axially thicker than the commissure locations, or uniform all around the circumference.

FIG. 1 illustrates the dual nature of the valve delivery handle 10 in that it provides both a portion of the handle of the delivery system, as well as a through lumen that leads directly through the holder 22 and a leaflet parting member (described below) to the space within the anchoring skirt 32. Although not shown, other elements of the delivery system mate with the proximal coupler 14 to provide an elongated access channel for delivery of an expander such as a balloon to a space within the anchoring skirt 32.

The surgeon advances the heart valve 20 until it rests in a desired implant position at the aortic annulus AA. The undulating suture-permeable ring 38 desirably contacts the ascending aorta AO side of the annulus AA, and is thus said to be in a supra-annular position. Such a position enables selection of a larger orifice prosthetic valve 20 as opposed to placing the ring 38, which by definition surrounds the valve orifice, within the annulus AA, or infra-annularly. Further details of the delivery procedure are shown and described in U.S. Pat. No. 8,641,757, filed Jun. 23, 2011, the contents of which are expressly incorporated herein.

After seating the prosthetic heart valve 20 at the aortic annulus AA, the anchoring skirt 32 is expanded into contact with a subvalvular aspect of the aortic valve annulus, such as with a balloon, to anchor the valve 20 to the annulus AA and seal a concentric space between aortic annulus/LVOT and bio-prosthesis so as to prevent paravalvular leaks. The operator then severs any retention sutures (not shown) between the holder 22 and valve 20, deflates the balloon and withdraws it along with the entire assembly of the leaflet parting member, holder 22 and valve delivery handle 10. Finally, the guide sutures 50 will be tied off to further secure the valve in place.

The inner stent frame 52 seen in detail in FIGS. 2A and 2B may be similar to an expandable stainless-steel stent used in the Edwards SAPIEN® Transcatheter Heart Valve. However, the material is not limited to stainless steel, and other materials such as Co—Cr alloys, nitinol, etc., may be used. In one embodiment, the radial thickness of the plurality of struts is around 0.4-0.6 mm. In a preferred embodiment, the material used should have an elongation at break greater than 33%, and an ultimate tensile strength of greater than about 490 MPa. The stent frame 52 may be initially formed in several ways. For instance, a tubular portion of suitable metal such as stainless steel may be laser cut to length and to form the latticework of chevron-shaped interconnected struts. After laser cutting, the stent frame 52 is desirably electro-polished. Other methods including wire bending and the like are also possible. Following manufacture, and crimping, the inner stent frame 52 assumes a crimped, tapered configuration that facilitates insertion through the calcified native aortic valve (see FIG. 1).

It should be noted that the stent frame 52 in FIG. 2A commences at its upper end 62 in a generally tubular shape and then angles inwardly to be tapered toward its lower end 64. That is, the generally tubular portion has a height h which is only a portion of the total height H. As shown, the tubular portion has a height h which generally corresponds to the height between troughs **60*a* and the peaks 60*b* of an upper end 62 of the stent frame. The upper end 62 is preferably defined by a thicker wire for reinforcement. The upper end 62 follows an undulating path with alternating arcuate troughs 60*a* and pointed peaks 60*b* that generally corresponds to the undulating contour of the underside of the sewing ring 38 (see FIG. 3A). Desirably, the height h of the peaks 60*b* above the troughs 60*a*** is between about 25-36% of the total stent frame height H, with the ratio gradually increasing for larger valve sizes.

With reference still to FIG. 2A, the constricted stent frame 52 of the anchoring skirt 32 has an initial shape following manufacture in a tapered configuration with a lower (inflow/leading) end 64 defining a smaller first diameter $D_1$ orifice than that described by the upper (outflow/trailing) end 62. As mentioned, the anchoring skirt 32 attaches to an inflow end of the valve member 30, typically via sutures through the upper end 62 of the stent frame 52 connected to fabric on the valve member 30 or sewing ring 38. The particular sewing ring 38 as shown in FIG. 3A includes an undulating inflow contour that dips down, or in the inflow direction, in the regions of the valve cusps 33, and arcs up, in the outflow direction, in the regions of the valve commissures 34. This undulating shape generally follows the inflow end of the heart valve member wireform 50 (see FIG. 2) which seats down within the sewing ring 38. The scalloped upper end 62 of the stent frame 52 also conforms to this undulating shape, with peaks **60*b* aligned with the valve commissures 34 and valleys 60*a* aligned with the valve cusps 33**.

The mid-section of the frame 52 has three rows of expandable struts 66 in a sawtooth pattern between axially-extending struts 68. The axially-extending struts 68 are in-phase with the peaks **60*b* and troughs 60*a* of the upper end 62 of the stent frame. The reinforcing ring defined by the thicker wire upper end 62 is continuous around its periphery and has a substantially constant thickness or wire diameter interrupted by eyelets 70, which may be used for attaching sutures between the valve member 30 and skirt 32. Note that the attachment sutures ensure that the peaks of the upper end 62 of the skirt 32 fit closely to the troughs of the sewing ring 38**, which are located under the commissures of the valve.

As seen in FIG. 2B, the minimum diameter d of the upper end 62 of the covered skirt 32 will always be bigger than the ID (which defines the valve orifice and corresponding labeled valve size) defined by the prosthetic valve member 30 to which it attaches. For instance, if the upper end 62 secures to the underside of the sewing ring 38, which surrounds the support structure of the valve, it will by definition be equal to or larger than the ID or flow orifice of the support structure. Typically, however, the upper end 62 attaches via sutures to fabric covering an inner stent structure (not shown), one part of which is the inner polymer band 44.

FIG. 2B illustrates the stent frame 52 isolated and in its expanded configuration. Balloon inflation is designed to expand only the inflow or lower end 64 of the frame, and no expansion loads are exerted on the outflow or upper end 62 to prevent damage to the supra-annular elements of the valve, and therefore the supra-annular valve remains dimensionally unchanged. The inflow end 64 of the prior art stent frame 52 is designed to expand symmetrically and radially as the balloon inflates. The lower end 64 has a diameter $D_2$ which is larger than the diameter of the upper end 62. The expanded shape of the stent 52 is also preferably slightly flared outward toward its lower end 64, as shown, by virtue of expanding with a spherical balloon. This shape helps the stent conform to the subvalvular contours of the left ventricle, below the aortic valve, and thus helps anchor the valve in place.

Conduction System of the Heart

As mentioned above, it is important to ensure that the expanding stent frame 52 seals well the space between the implant and the LVOT and it does not impinge on the conduction system of the heart, therefore affecting its function. Indeed, such a concern is not limited to the hybrid prosthetic heart valve 20 illustrated herein, but applies to any expandable valves, in particular those with balloon-expandable stents.

Figure 3:
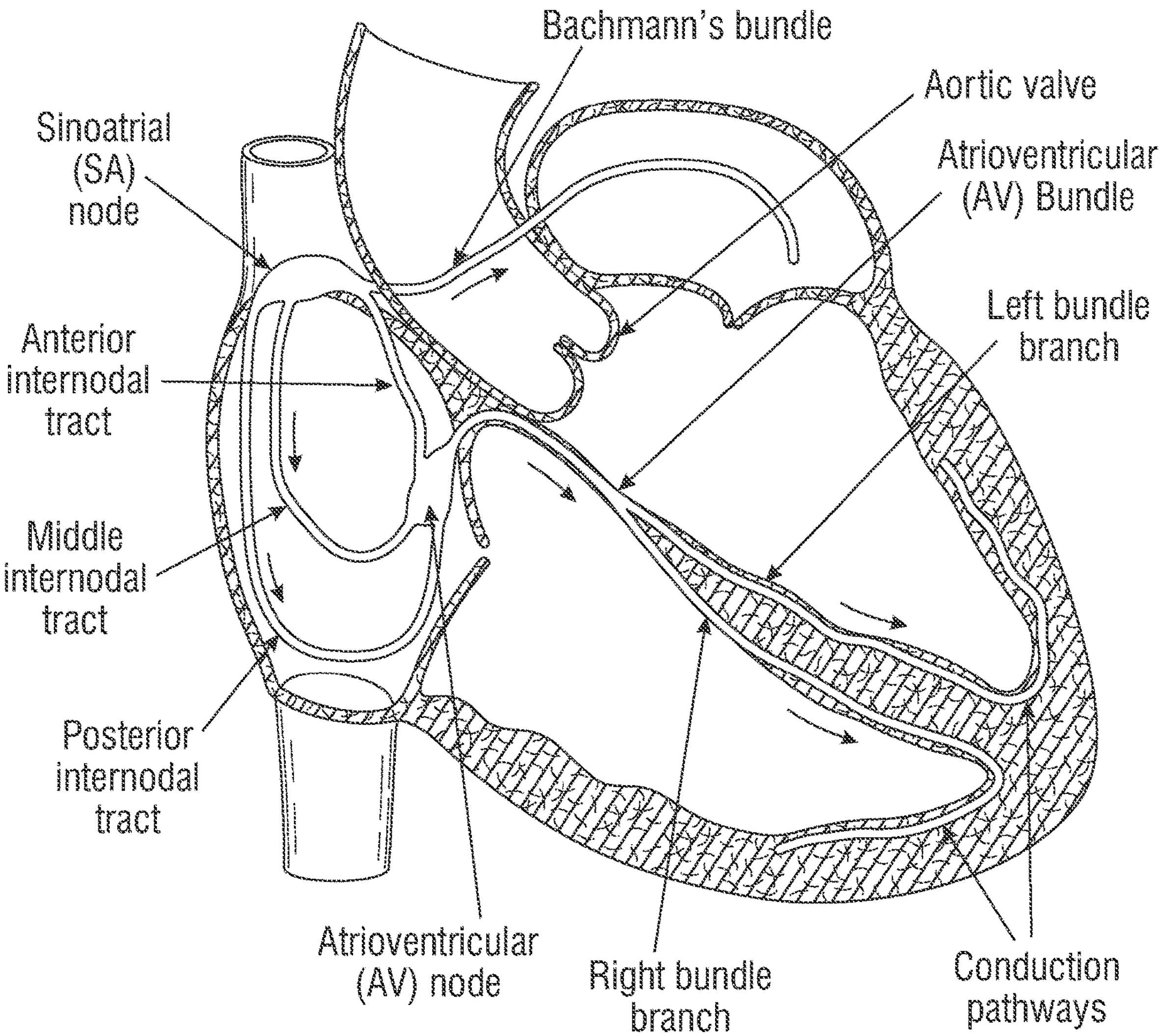
FIG. 3 is a schematic diagram of the conduction system of the heart with primary features labeled.

As seen in FIG. 3, the conduction system of the heart is not uniformly distributed around the native heart valves, but instead is concentrated in several regions. The cardiac conduction system or impulse conduction system of the heart generally consists of four structures: 1. The sinoatrial node (SA node) 2. The atrioventricular node (AV node) 3. The atrioventricular bundle (AV bundle) bifurcated into left and right branches, and 4. The Purkinje fibers in the wall of the heart muscle (not illustrated). The cardiac muscle fibers that compose these structures are specialized for impulse conduction rather than the normal specialization of muscle fibers for contraction. The impulses commence at the SA node which is sometime described as the heart's pacemaker and is located at the upper portion of the right atrium. From there, signals transmit through internodal tracts to the AV node located in the lower part of the right atrium, through the AV bundle in the central fibrous tissue between the chambers, and to the fibers in the left and right ventricular myocardial tissue.

FIG. 3 shows the AV node adjacent the aortic valve. A conduction bundle (Bundle of His) traverses a membranous septum to an interventricular septum. During its course, a Left bundle branch is closer to the Right Coronary annulus and innervates the left ventricle through fascicles and Purkinje fibers. The Right bundle branch exits from membranous septum, penetrates the upper part of the septum and on to the right side of the interventricular septum, leading to the right ventricle and its fascicles and Purkinje fibers. Numerous anatomical studies have attempted to map the course of these conductive fibers in and around the heart's chambers.

Figure 4:
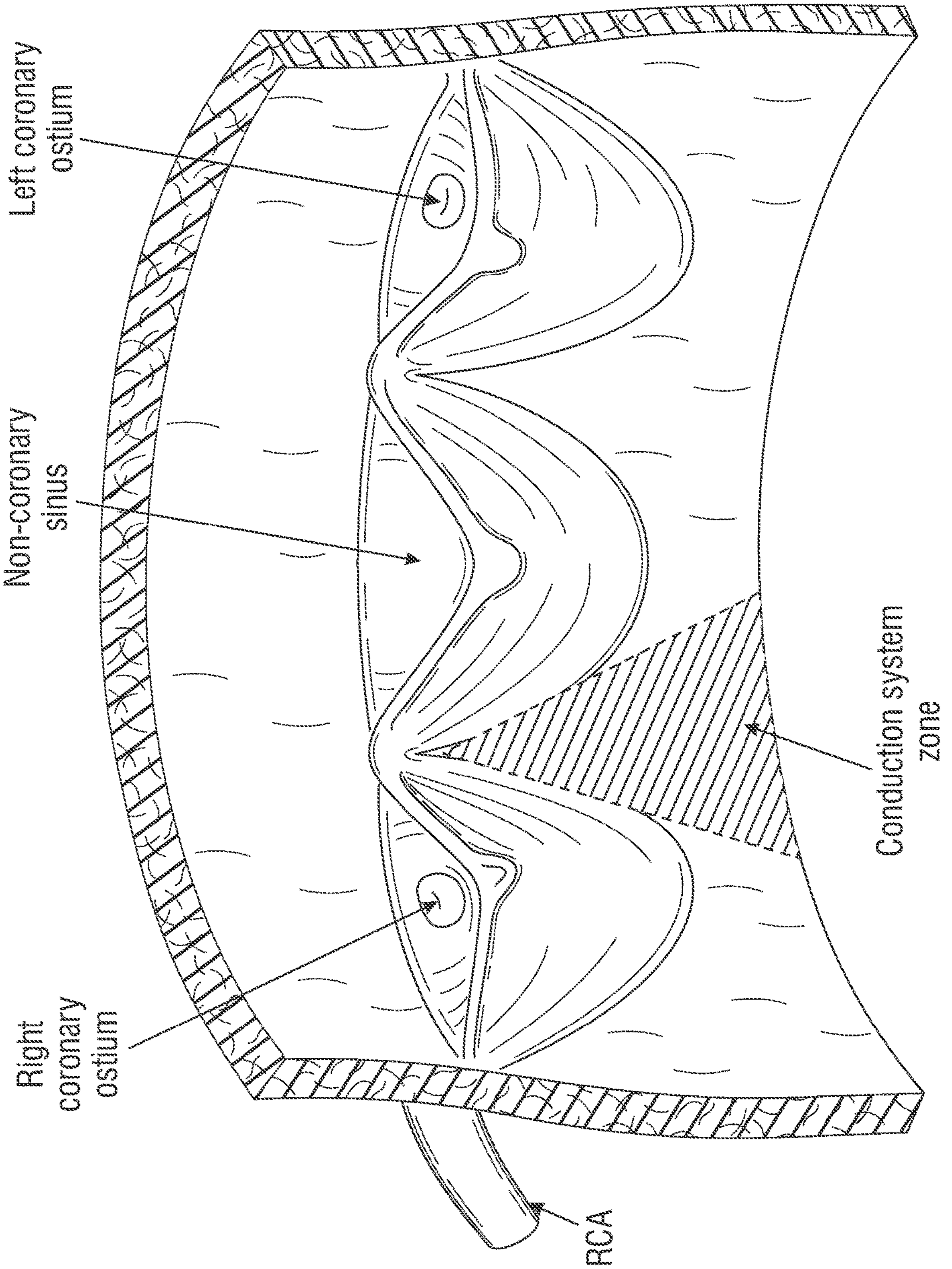
FIG. 4 is a laid-flat image of the aortic valve showing the general location of the adjacent conduction system zone.

With reference to laid-flat depiction of the aortic valve in FIG. 4, the conductive pathway adjacent the aortic valve is typically understood to be located in a subvalvular region between the right coronary sinus and the non-coronary sinus. This conduction system zone is depicted schematically as a triangular area extending up between the two sinuses and expanding downward into the left ventricle. The precise location, depth and lateral span of the conduction system zone varies between patients, though the zone commences at a depth below the annulus where the Bundle of His emerges, and that depth is believed to decrease in those with aortic stenosis. Some clinical results demonstrate that the shorter the depth below which the Bundle of His emerges, the higher the risk of conduction abnormalities. A longer depth, on the other hand, indicates a longer distance from the annulus to the Bundle of His, which may allow longer and wider heart valve implants without necessarily causing conduction abnormalities.

Figure 5:
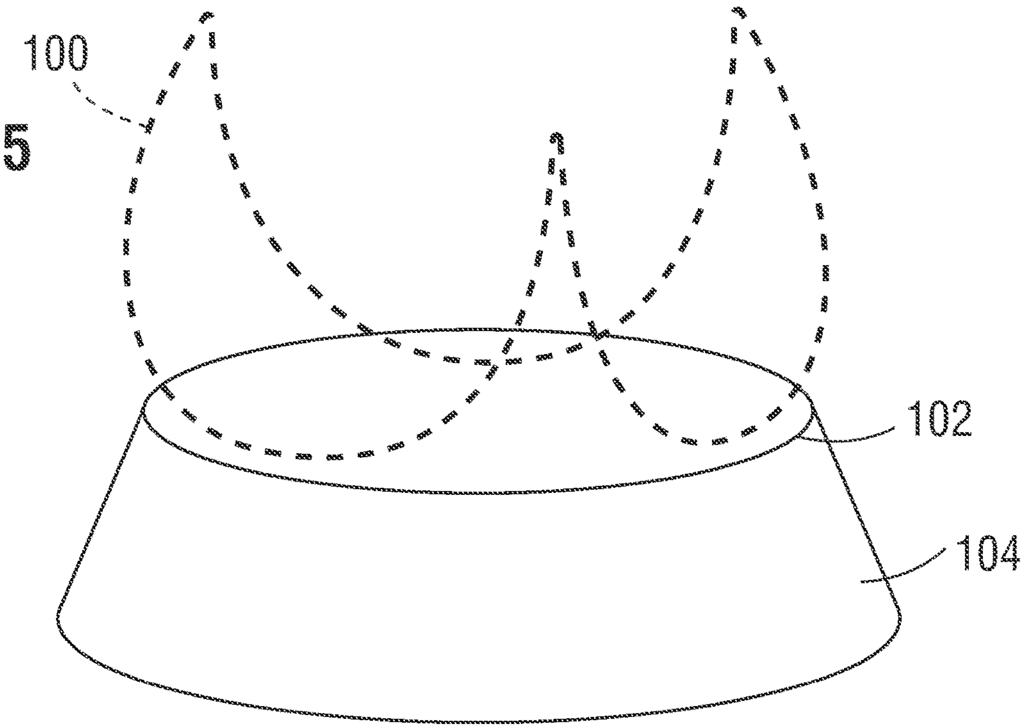
FIG. 5 is a schematic representation of the outline of a hybrid prosthetic heart valve.

FIG. 5 illustrates the outlines of a typical hybrid prosthetic heart valve, such as the valve 20 shown in FIG. 2. A dashed line 100 indicates the undulating shape of the support structure for the three flexible leaflets. The lower circle 102 is an imaginary line connecting the lower arcuate cusps of the support structure, which is intended to be located at the lower ends of the coronary sinuses when implanted. The two lines 100, 102 generally describe the outline of a conventional surgical valve. The lower conical shape indicated at 104 corresponds to the footprint of an expanded subvalvular stent or skirt, such as the skirt 32 shown for the valve 20 in FIG. 2.

Figure 6:
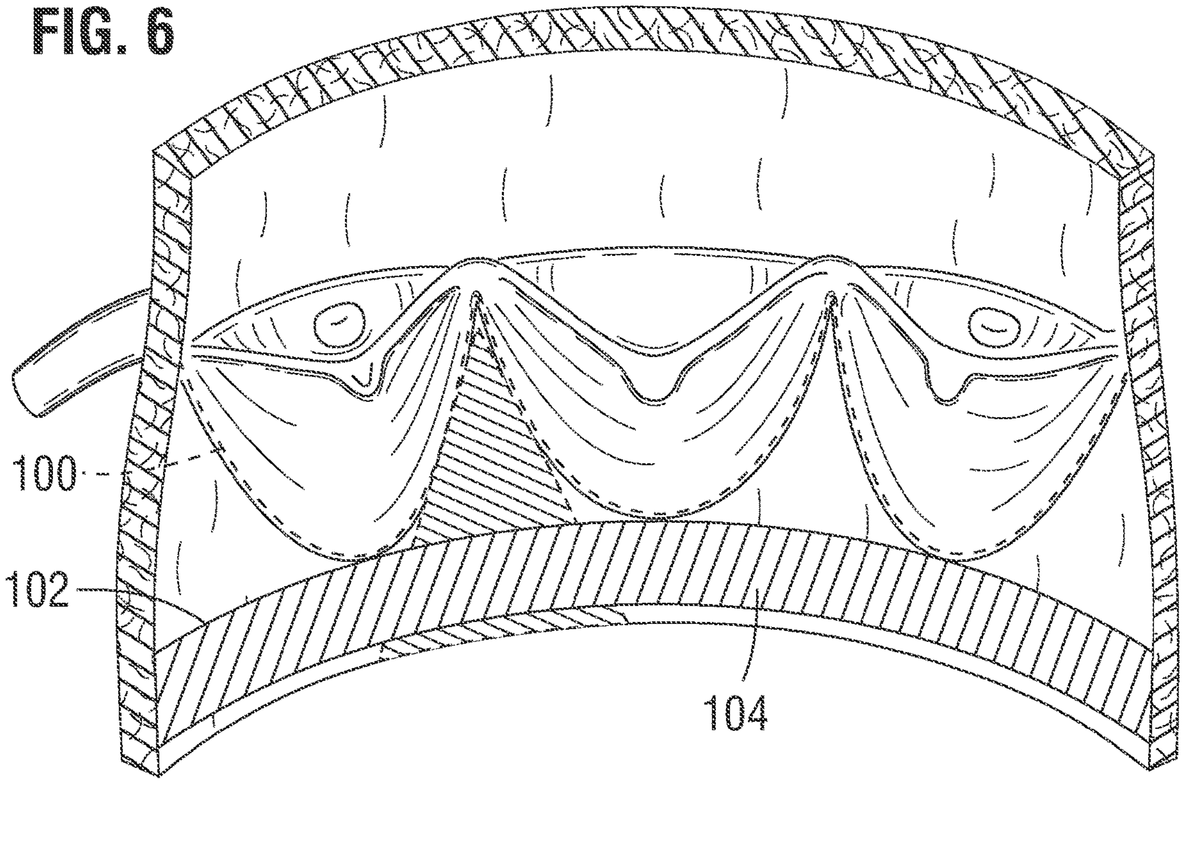
FIG. 6 is a laid-flat image of the hybrid prosthetic heart valve outline of FIG. 5 superimposed over the laid-flat image of the aortic valve of FIG. 4.

Now with reference to FIG. 6, the same general outlines of the hybrid prosthetic valve from FIG. 5 are superimposed on the laid-flat aortic annulus as if implanted. The three upstanding posts of the valve defined by dashed line 100 extend up between the three sinuses—right, non-coronary, and left. The lower circle 102 extends just below the sinuses, and the subvalvular skirt shape 104 lies against the inside of the left ventricle. This superposition illustrates where possible sources of interference with the conduction system zone are located. That is, expansion of the skirt 32 into the triangular conduction system zone (hatched area) between the right coronary sinus and the non-coronary sinus may impact the heart's conduction system.

Figure 7:
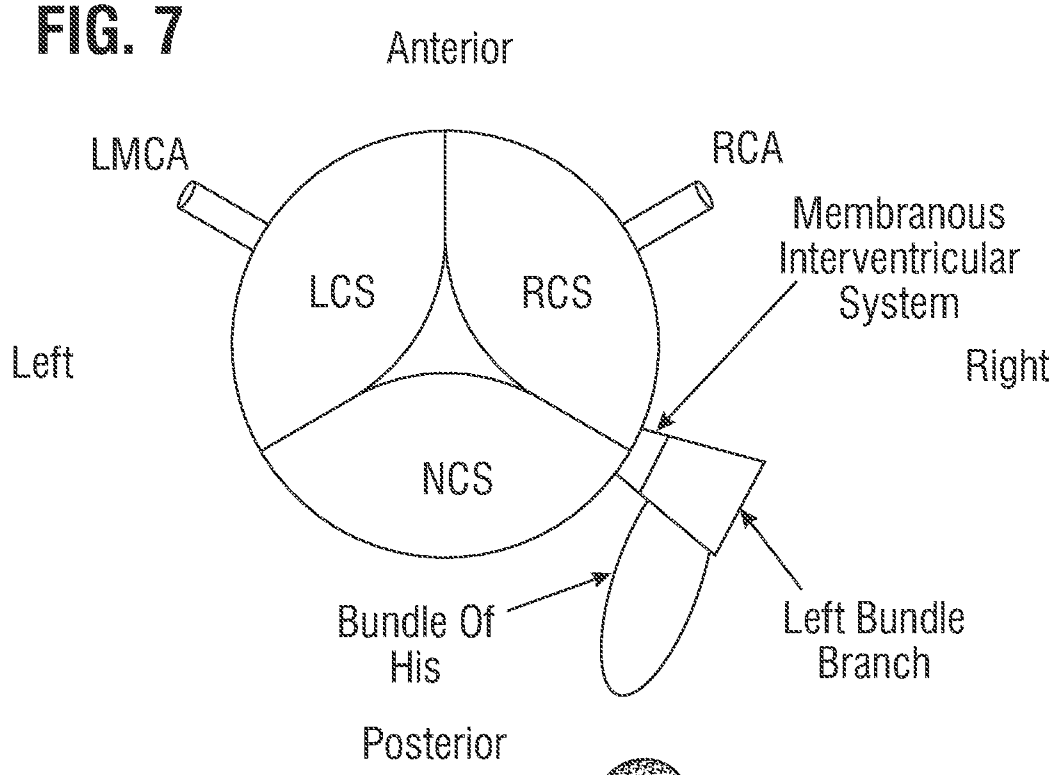
FIG. 7 is a schematic plan view of an aortic valve indicating the location of the adjacent conduction system components.

FIG. 7 is a schematic plan view of an aortic valve indicating the approximate location of the adjacent conduction system components. Namely, the Left bundle branch and Bundle of His are embedded in the cardiac tissue just outside of the membranous interventricular septum on the posterior side of the aortic valve. As stated above, the normal position of the conduction system components is adjacent the valve commissure between the right coronary sinus or cusp (RCS) and the non-coronary sinus or cusp (NCS). This location helps inform modifications to prosthetic valves, as set forth below.

Hybrid Heart Valve Modifications

Figure 8:
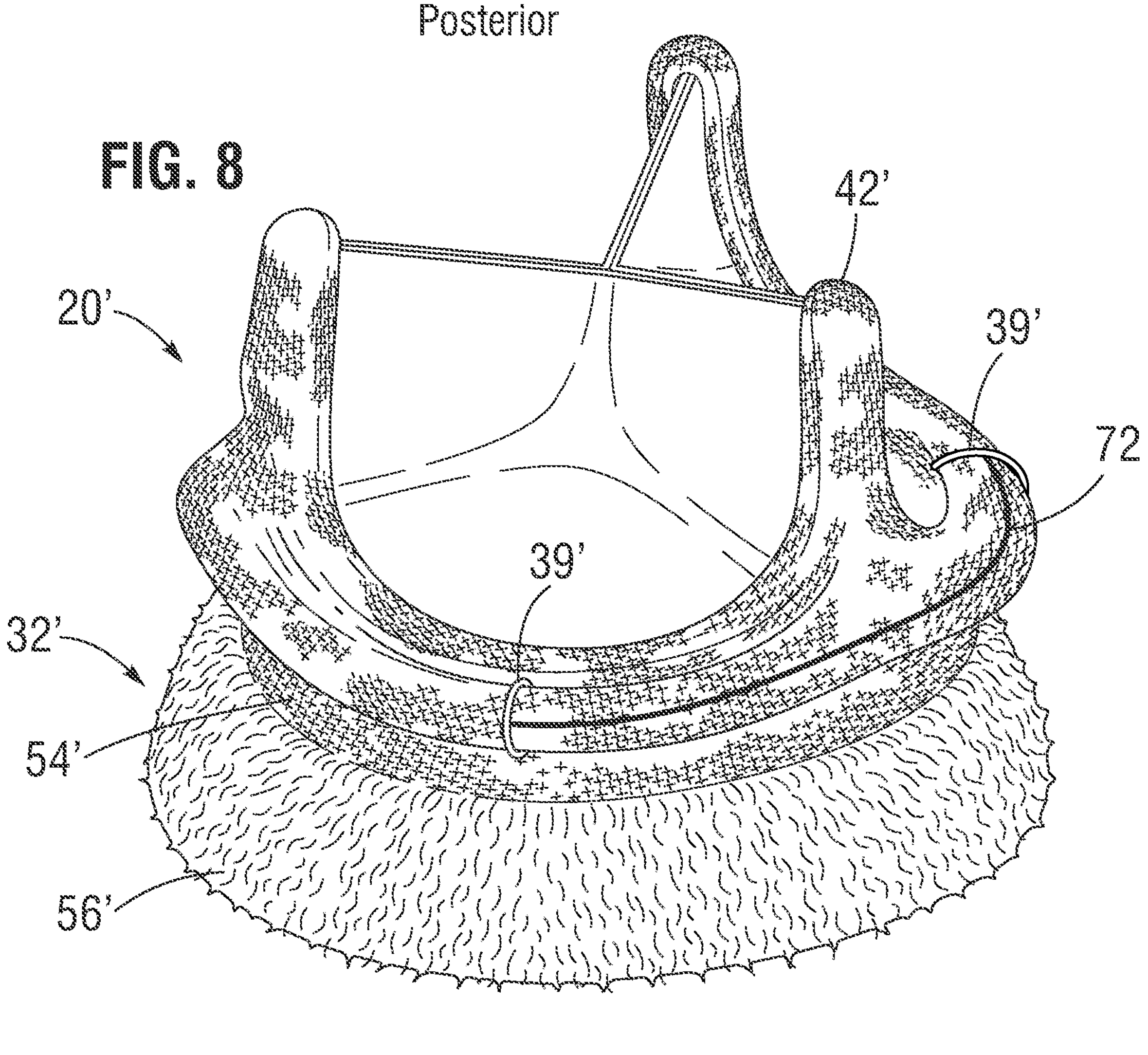
FIG. 8 is a perspective view of an assembled hybrid prosthetic heart valve showing marking on the exterior thereof to indicate rotational placement when implanting the valve.

FIG. 8 is a perspective view of an assembled hybrid prosthetic aortic heart valve 20' modified to avoid interference with the heart's conduction system. In particular, the expandable skirt 32' will be modified as explained below. A preferred modification involves modification of an inner stent frame of the skirt 32' around only a portion of the circumference thereof. The portion modified corresponds to a portion that will be implanted adjacent the conduction system, or generally adjacent the valve commissure between the right coronary sinus or cusp (RCS) and the non-coronary sinus or cusp (NCS), as seen in FIG. 7. To guide the surgeon during implant of the valve 20', markings on the exterior thereof are provided to indicate rotational placement. That is, the surgeon can discern the anatomical features around the aortic valve visually, but the portion of the stent frame that is modified will not be apparent due to the outer cloth coverings 54', 56'.

Conventional aortic heart valves typically have three distinct markings around their periphery that indicates to the surgeon the cusp regions 33, as seen at 39 in FIG. 2. In particular, thick black marker thread is used to form the markings 39. The modified valve 20' also has the three cusp markings 39', as well as a distinct elongated marking 72 extending between two of the cusp markings 39'. The elongated marking 72 thus extends around ⅓ of the way (120°) around the modified valve 20' and is aligned with a modified arcuate span of the stent frame of the skirt 32'. When the surgeon implants the valve 20', he or she rotates the linear marking 72 to align with that portion of the anatomy in which is located the conduction system. As explained above with reference to FIG. 7, the conduction system is expected to be located adjacent the valve commissure between the right coronary sinus or cusp (RCS) and the non-coronary sinus or cusp (NCS). Thus, the arcuate marking 72 is centered on the valve commissure post 42'. The elongated marking 72 may be formed by a printed indicator, or by sewing one or more lengths of suture along the appropriate area. The elongated marking 72 is colored so as to contrast highly with the sealing ring 38', such as a black marker suture against a white cloth covering. Bright or fluorescent colors may also be used to be more visible in dim lighting.

Figure 9A:
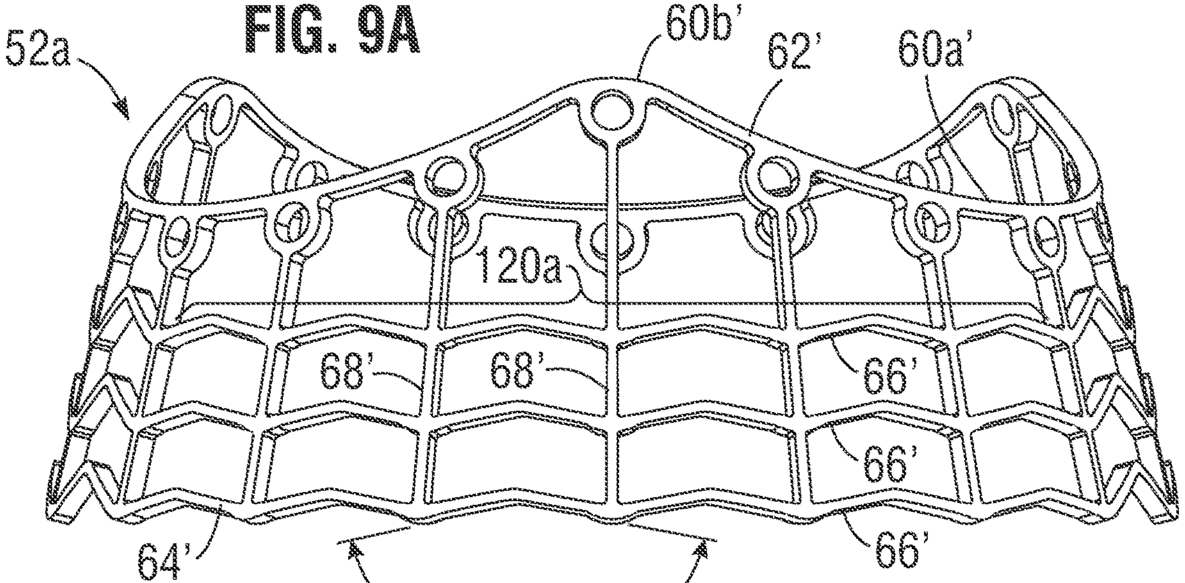
FIGS. 9A-9C are elevational views of exemplary stent frames of the present application for use in an anchoring skirt of a hybrid prosthetic heart valve, the stent frames shown radially expanded with struts modified to reduce impact on an adjacent heart conduction system.
Figure 9B:
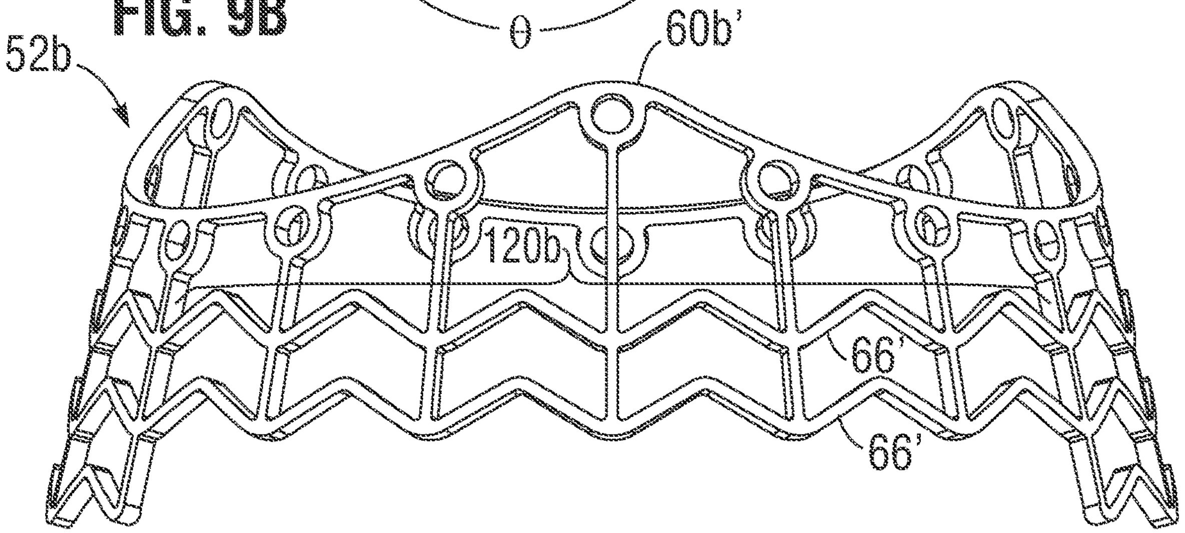
Figure 9C:
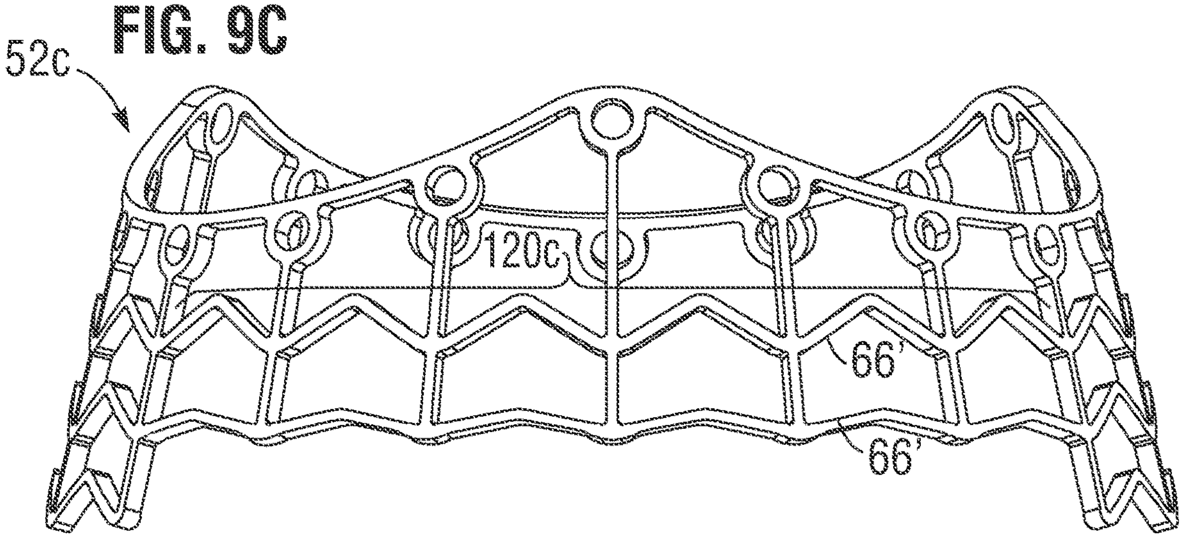

FIGS. 9A-9C are elevational views of exemplary stent frames 52*a*, 52*b*, 52*c* of the present application for use in an anchoring skirt of a hybrid prosthetic heart valve, the stent frames are shown radially expanded with struts modified to reduce impact on an adjacent heart conduction system. It should be noted that the stent frames are constructed generally the same as with the stent frame 52 of FIG. 2A, described above, aside from the modifications below, and thus like elements will have like numbers with the addition of a prime (e.g., 62').

In FIG. 9A, the stent frame 52*a* is shown with a thicker wire upper end 62' having an undulating periphery with alternating troughs 60*a*' and the peaks 60*b*'. The stent frame 52*a* when constricted has a generally tubular shape at its upper end 62' and then angles inwardly to be tapered toward its lower end 64'. When expanded, the lower end 64' expands radially outward as shown, with a flared configuration. As before, a mid-section of the frame 52*a* has three circumferential rows of expandable struts 66' in a sawtooth pattern with V-shaped bends between axially-extending struts 68'. The axially-extending struts 68' are in-phase with the peaks 60*b*' and troughs 60*a*' of the upper end 62' of the stent frame.

In a region 120*a* (bracketed) of the stent frame 52*a* centered on one of the peaks 60*b*', the three rows of expandable struts 66' exhibit shallower (greater) included angles θ in the bends of the sawtooth pattern in the expanded state of the stent frame 52*a* than in the rest of the frame. More precisely, the bends are shallower in the region 120*a* that extends about 120° between two of the troughs 60*a*'. Generally, the region 120*a* may extend circumferentially between about 90-120°. In an exemplary embodiment, the included angles of the bends in the region 120*a* are between about 135-160°, while the bends in the rows of expandable struts 66' around the rest of the stent frame are between about 45-90°. The result is that the rows of expandable struts 66' in the region 120*a* expand less than around the rest of the stent frame 52*a* when caused to straighten out and lengthen. In other words, they straighten out faster, as shown by the final angle θ of the bends in the expanded frame versus the rest of the bends. This produces an asymmetric expansion of the stent frame 52*a*, with about ⅔ of the frame expanding normally and about ⅓ expanding less. The region 120*a* forms something of an arcuate chordal shape when expanded, extending between circular adjacent regions, as seen best in FIG. 12B.

It should be noted that the final angle θ of the bends in the expanded frame 52*a* is typically the same bend angle of the stent frame in region 120*a* when initially formed. That is, the frame 52*a* is fabricated in a tubular shape, then crimped down to a smaller diameter prior to packaging and shipping, as the stent frame is delivered in the contracted state. Consequently, the final bend angles θ of the frame 52*a* are set at the time of frame formation. One method of frame construction is laser-cutting the various struts from a tubular blank of plastically-expandable material such as stainless steel or an elastic material such as nitinol.

In one embodiment, the majority of the stent frame 52*a* is configured to normally flare outward to a maximum diameter that is several millimeters greater than the nominal heart valve size. The "nominal heart valve size" means the labeled heart valve size selected for that particular annulus, and generally corresponds in odd mm increments to the measured diameter of the naïve heart valve orifice. The "nominal heart valve size" is also slightly less than the diameter d of the upper end 62' of the stent frame 52*a*. For example, the "nominal heart valve size" may be 21 mm, and the lower end 64' of the stent frame 52*a* flares outward to a maximum diameter of about 23.5 mm. However, the region 120*a* of the stent frame 52*a* centered on one of the peaks 60*b*' is configured to expand outward by between 1-2 mm less, or to a diameter of between about 21.5-22.5 mm. This helps reduce the force applied to the surrounding subvalvular region where the conduction system is assumed to be.

In another solution to potential impaction on the conduction system, FIG. 9B shows a stent frame 52*b* with a lower circumferential row of expandable struts 66' removed in the region 120*b* (bracketed) of the stent frame 52*b* centered on one of the peaks 60*b*'. In the illustrated embodiment, as with the stent frame 52*a*, the region 120*b* extends around ⅓ of the periphery of the stent frame between cusps, or about 120°. More generally, the region 120*b* may extend circumferentially between 90-120°. The included angles of the bends in the region 120*b* remain as in the rest of the frame, between about 45-90°, and thus that portion of the region 120*b* with circumferential struts 66' expands normally. As mentioned above, in some patients the electrical conduction system adjacent the aortic valve does not commence until some ways down into the left ventricle, in which case expansion of the stent frame 52*b* may avoid even contacting that zone.

Finally, FIG. 9C shows a third alternative stent frame 52*c* which also has the lower circumferential row of expandable struts 66' removed in the region 120*c* (bracketed). In addition, the next adjacent circumferential row of expandable struts 66' in the region 120*c* has shallow included bend angles in the expanded state of the stent frame 52*c*, such as in the range stated above for the included angles of the bends for the stent frame 52*a* of FIG. 9A. Thus, when the stent frame 52*c* expands, the conduction system zone may be avoided altogether because of the missing lower row, and the next adjacent row of struts 66' expands less than the rest of the stent frame (e.g., asymmetric radial expansion) which reduces outward pressure on that zone. As before, the region 120*c* preferably extends circumferentially between about 90-120° between two of the troughs 60*a*' and is centered on one of the peaks 60*b*'.

Figure 10:
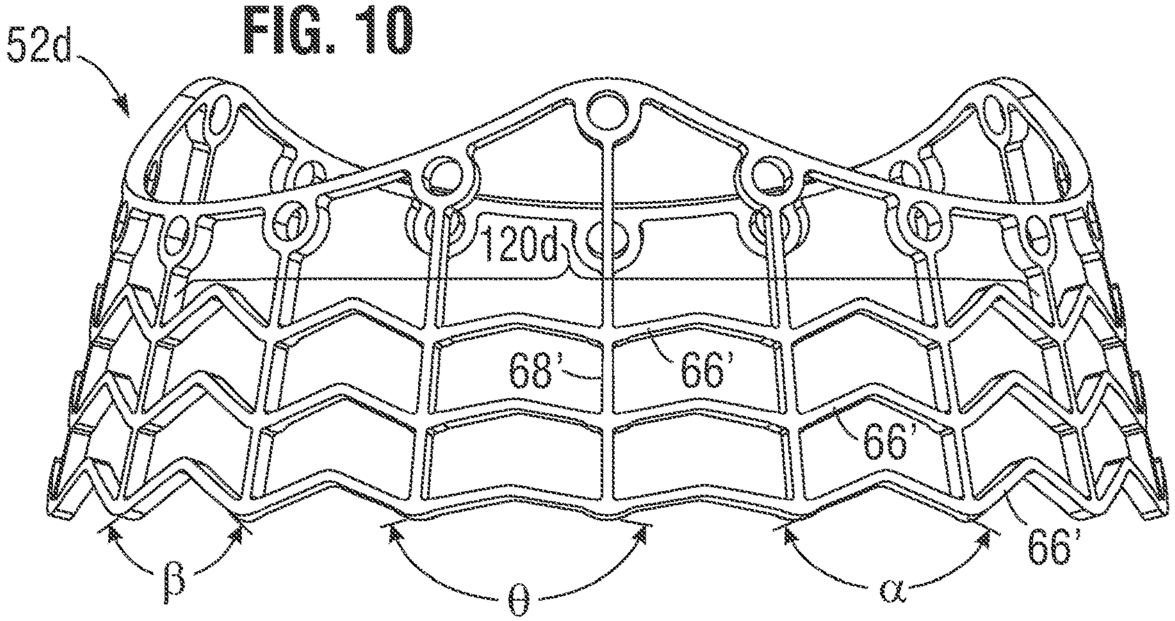
FIG. 10 is an elevational view of another exemplary stent frame radially expanded with struts modified to reduce impact on an adjacent heart conduction system.

FIG. 10 is an elevational view of another exemplary stent frame 52*d* radially expanded with struts modified to produce asymmetric expansion around the skirt. In this embodiment, the lower circumferential row of expandable struts 66' in a region 120*d* (bracketed) has variable included bend angles, with shallower angles toward the center of the region 120*d*. In particular, there may be eighteen axially-extending struts 68' in-phase with the peaks 60*b*' and troughs 60*a*' of the upper end 62' of the stent frame, which means there are six in each ⅓ dividing the region 120*d* into six spans across which there are the bends in the expandable struts 66'. The inner two spans have shallow (large) bend angles, while the next two outward spans have smaller bend angles, and the outermost two spans have even smaller bend angles. The inner two spans straighten the fastest, as shown by the final angle bend angles θ, the next two outward spans straighten less as seen by final bend angles α, and the outermost two spans have more room for expansion, as seen by their final bend angles β. This alters the asymmetric expansion such that the reduction in final diameter in the region 120*d* is gradual from the adjacent unaltered regions. More particularly, in comparison with a more chordal shape between the adjacent regions, as with the embodiment of FIG. 9A, the expanded shape of the region 120*d* is more rounded, closer to the circular shape of the rest of the stent frame 52*d*. This focuses the expansion reduction in the center of the region 120*d*, which again may extend circumferentially between 90-120°. Of course, the particular pattern of variance of the included bend angles may differ, and the illustrated embodiment is only exemplary.

Figure 11A:
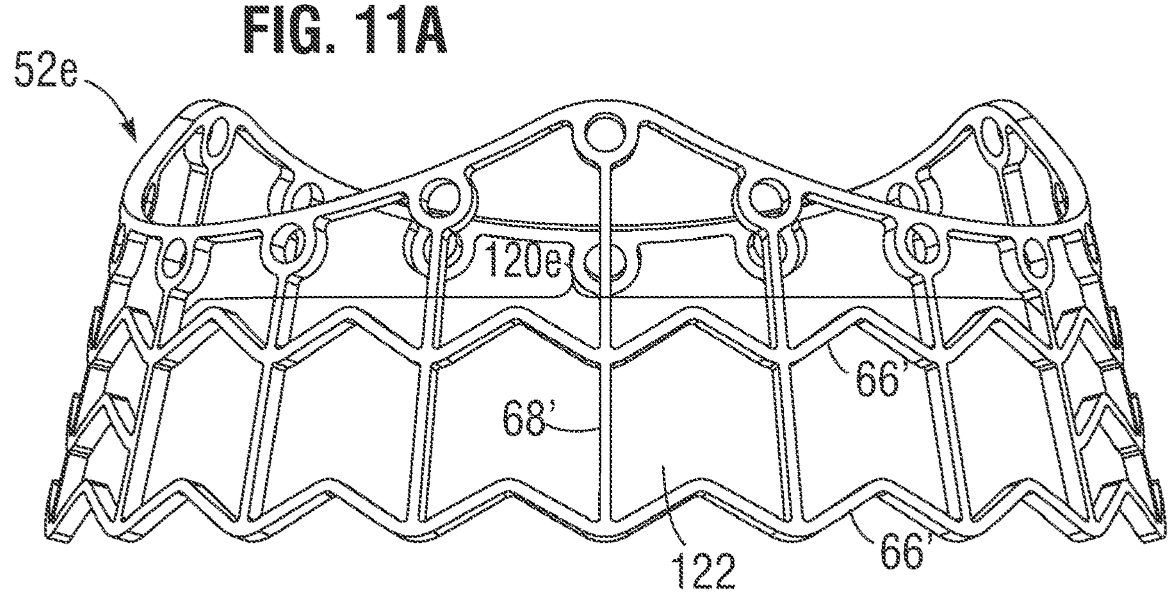
FIGS. 11A and 11B are elevational views of a further exemplary stent frame shown radially expanded with struts modified to reduce impact on an adjacent heart conduction system.
Figure 11B:
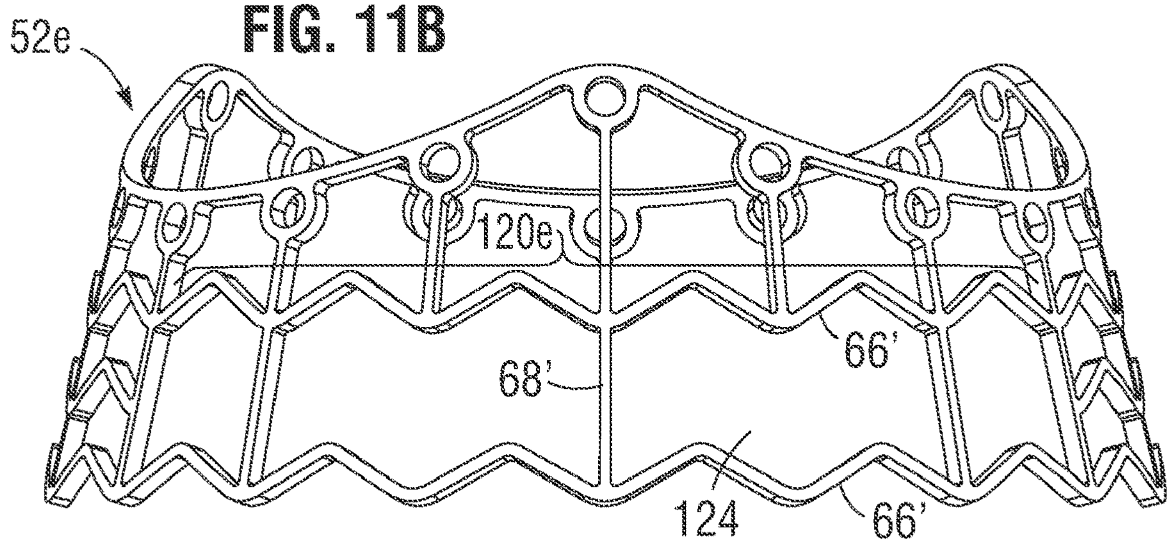

FIGS. 11A and 11B are elevational views of a further exemplary stent frame 52*e* shown radially expanded with a middle circumferential row of expandable struts 66' removed in a region 120*e* (bracketed) to reduce impaction on an adjacent native conduction system zone. FIG. 11A shows all of the axially-extending struts 68' retained to create a plurality of enlarged spaces or cells 122 between struts, while in FIG. 11B some of them are removed to create a plurality of even larger cells 124. In both stent frames 52*e*, the region 120*e* is desirably centered on one of the peaks 60*b*' and preferably extends circumferentially about 120°, more generally between 90-120°. These embodiments thus create larger cells or voids within the region 120*e* which, though expanded normally, reduces direct stent contact with the surrounding native conduction system zone. Of course, the included bend angles in the remaining rows of expandable struts 66' in the region 120*e* may also be shallow, as described above, to produce asymmetric radial expansion and further reduce the impact on the conduction system.

Figure 12A:
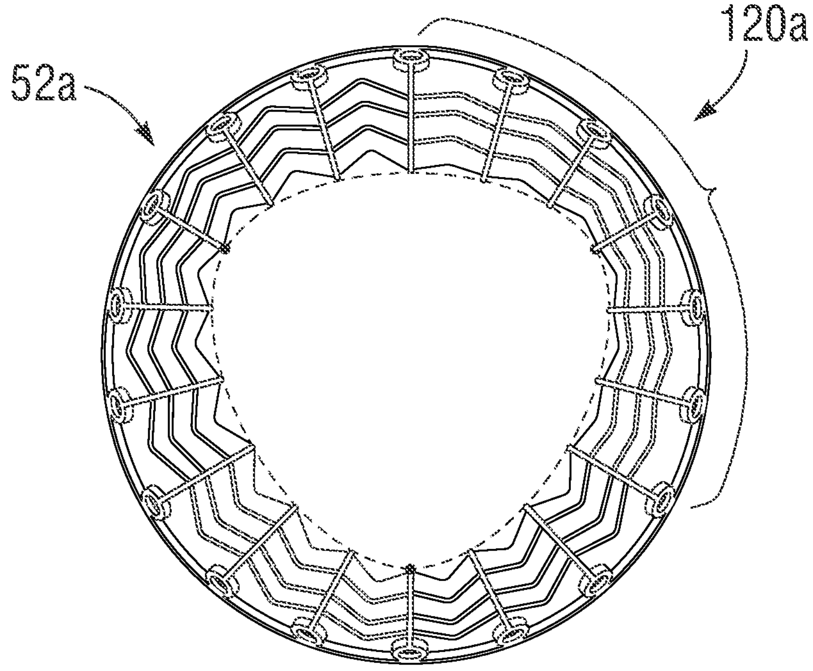
FIG. 12A shows a still further exemplary stent frame from below prior to expansion.
Figure 12B:
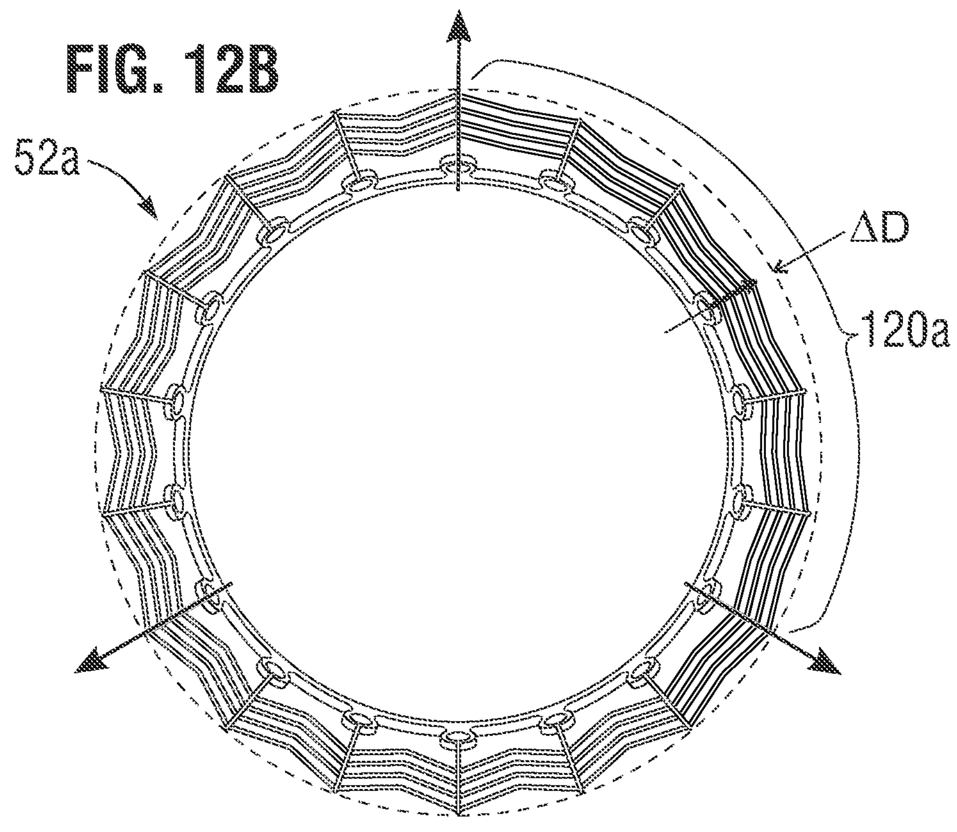
FIG. 12B shows the stent frame after expansion showing how one side does not expand as far as the remainder.

FIG. 12A shows the stent frame 52*a* from below prior to expansion, and FIG. 12B shows the stent frame 52*a* after expansion showing how one side does not expand as far as the remainder (e.g., asymmetric radial expansion). In particular, the region 120*a* includes the shallower included bend angles θ than in the rest of the stent frame 52*a*, and thus balloon expansion causes that region 120*a* to expand more in an arcuate chordal shape than circular, as with the remainder of the stent frame periphery. The distance ΔD from an imaginary circle drawn around the maximum diameter expansion is the preferred reduction in expansion diameter in the region 120*a*. As mentioned above, distance ΔD is preferably between 1-2 mm, and more preferably about 1.5 mm. Such a small reduction of expanded diameter in the asymmetric region 120*a* is believed sufficient to reduce negative impacts on the conduction system.

Fully-Expandable Heart Valve Modifications

Figure 13:
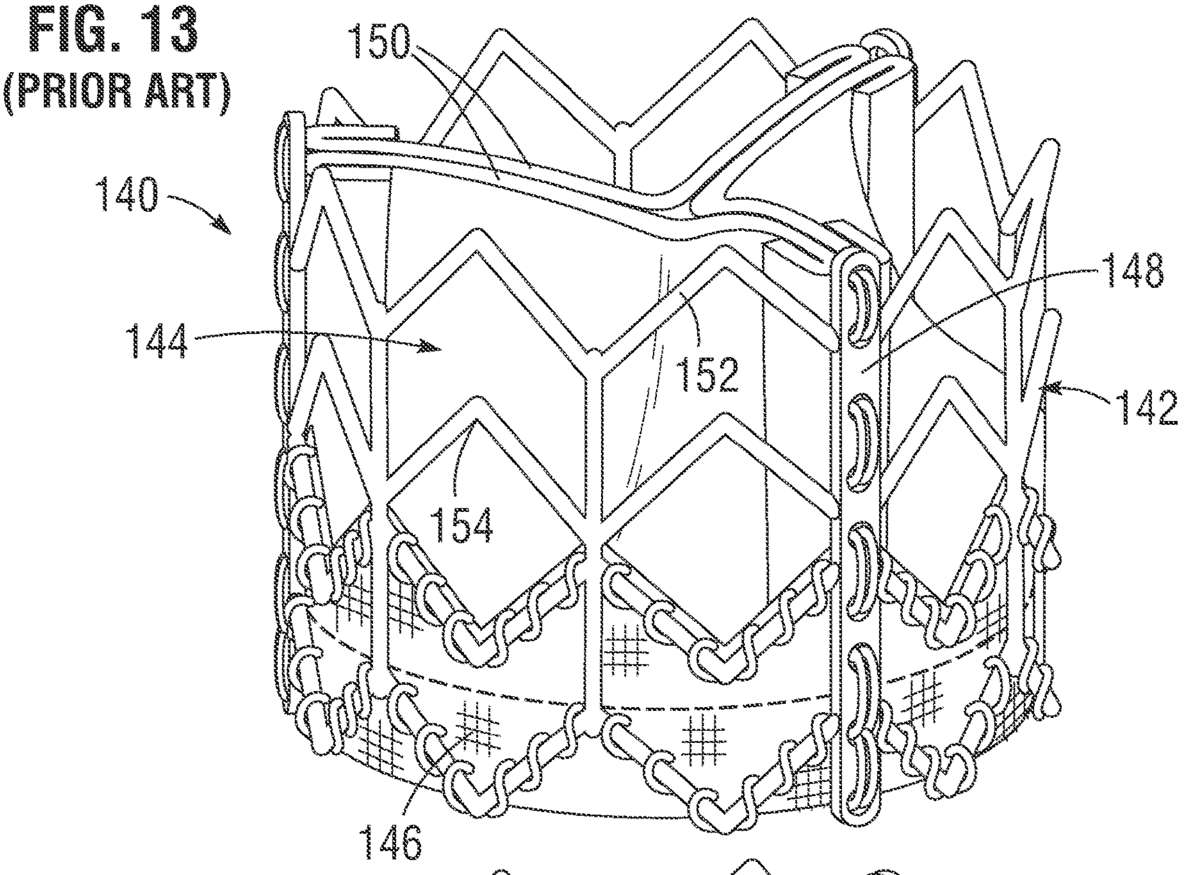
FIG. 13 (PRIOR ART)
FIG. 13 is a perspective view of a fully-expandable prosthetic heart valve of the prior art shown expanded.

FIG. 13 is a perspective view of a fully-expandable prosthetic heart valve 140 of the prior art shown expanded. The heart valve 140 is representative of a number of such valves, in particular the Sapien® line of valves sold by Edwards Lifesciences of Irvine, Calif. The heart valve 140 includes a structural frame 142 defining a flow passage therein and a plurality of flexible leaflets 144 secured within the frame, typically via suturing to an intermediate fabric skirt 146. In the illustrated embodiment, there are three of the leaflets 144 that meet at commissure posts 148 defined by the frame 142. The leaflets 144 extend axially within the frame 142 at the commissure posts 148 and adjacent leaflets abut each other and are sewn together along the posts. Cusp edges (not shown) of the leaflets 144 are also sewn to the frame 142. Free edges 150 of the leaflets 144 come together or coapt in the flow passage to form the one-way valve.

The structural frame 142 is fully expandable from a contracted configuration to the expanded shape shown. In this way, the contracted valve 140 may be advanced through a narrow passage into position at the target annulus, such as through a catheter or other delivery, without needing to stop the heart and put the patient on cardiopulmonary bypass. The contracted valve 140 is then expelled from the catheter or other delivery tube and expanded into contact with the annulus. The frame 142 may be self-expanding, or as in the case of the Sapien® line of valves, is balloon-expandable, such as being made of stainless steel. The frame 142 typically has a plurality of circumferential struts 152 with bends 154 that straighten out when the valve 140 expands. Prior art valves of this type have a tubular frame in both the contracted and expanded configurations stemming from a symmetrical distribution and shape of the circumferential struts 152.

Figure 14:
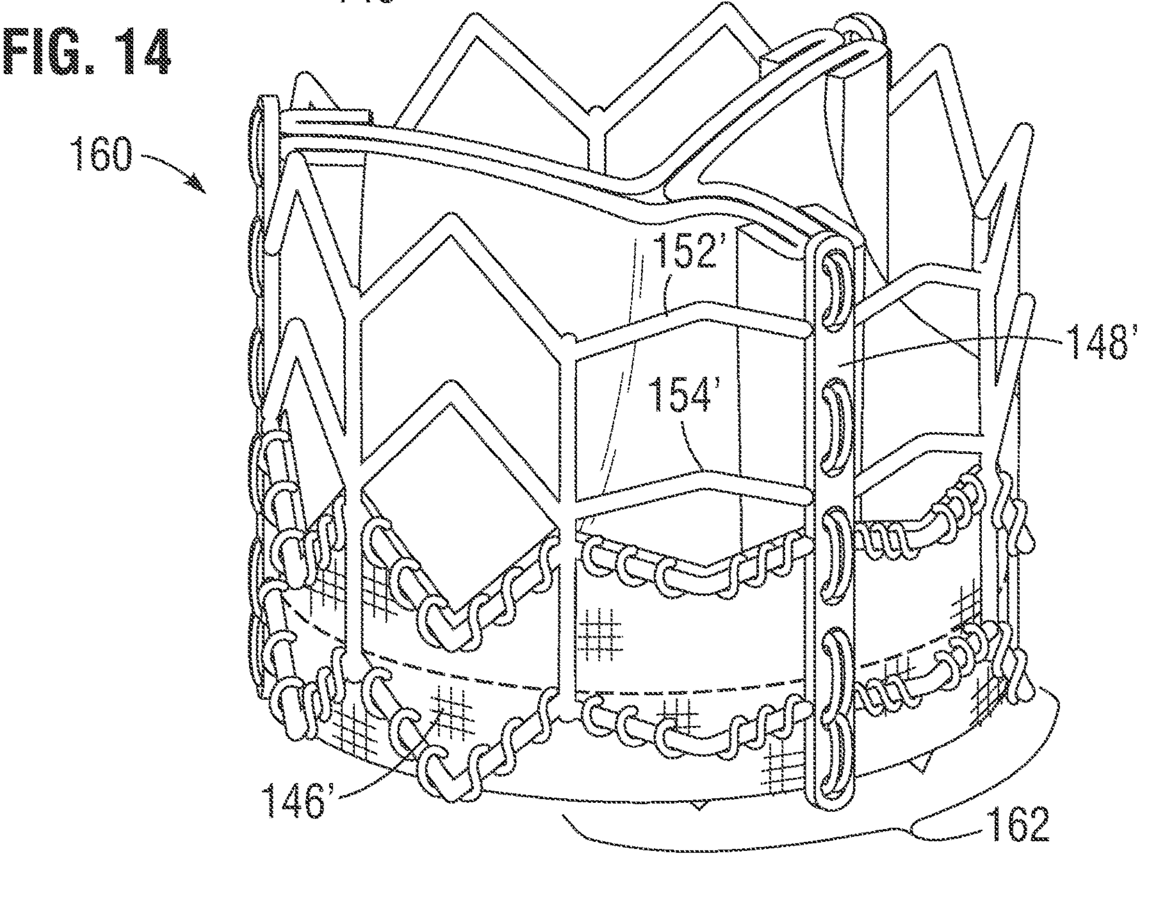
FIG. 14 is a perspective view of a modified fully-expandable prosthetic heart valve of the present application.

FIG. 14 is a perspective view of a modified fully-expandable prosthetic heart valve 160 of the present application. The valve 160 is in most respects the same construction as the representative heart valve 140 of FIG. 13, and so like elements are given like numbers with the addition of a prime (e.g., 142'). As before, the valve 160 comprises an expandable frame 142' supporting a plurality (e.g., three) flexible leaflets 144'. Once again, adjacent leaflets 144' are secured against each other at commissure posts 148' of the frame 142'.

The frame 142' has a circumferentially-extending region 162 (bracketed) in which the bends 156' in circumferential struts 152' have a much greater included angle then the bends 154' around the remainder of the frame. This modification reduces the amount of circumferential and thus radial expansion of the frame 152' in the region 162. This reduced or asymmetric expansion helps reduce contact with and thus impact on the adjacent conduction system of the heart when the valve 160 expands. If the heart valve 160 is intended for implant at the aortic annulus, the region 162 is centered at one of the commissure posts 148' as the conduction system is believed to be concentrated near one of the native commissures. To assist the surgeon in rotationally orienting the heart valve 160 during implant, a marker may be placed on either the appropriate commissure post 148' or on the fabric skirt 146' at that location. Although not shown, the marker may be as described above with respect to FIG. 8 (e.g., dark suture marker spanning 120°).

Figure 15:
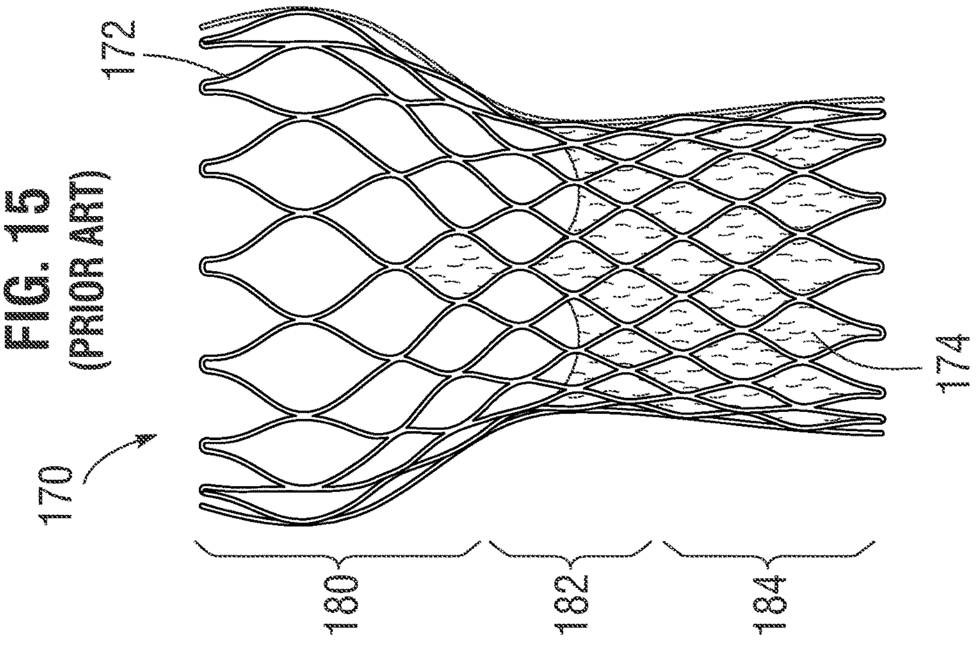
FIG. 15 (PRIOR ART)
FIG. 15 is an elevational view of another fully-expandable prosthetic heart valve of the prior art shown expanded.

FIG. 15 is an elevational view of another fully-expandable prosthetic heart valve 170 of the prior art shown expanded. The heart valve 170 generally comprises a self-expanding structural frame 172 having a tissue valve 174 sewn thereto. In one such embodiment, the Evolut™ TAVR System available from Medtronic Cardiovascular of Minneapolis, Minn. includes a supra-annular, self-expanding nitinol frame, with a porcine pericardial tissue valve. The structural frame 172 is somewhat hourglass-shaped and defines an enlarged upper region 180, a narrow middle region 182, and an enlarged lower region 184.

Figure 16:
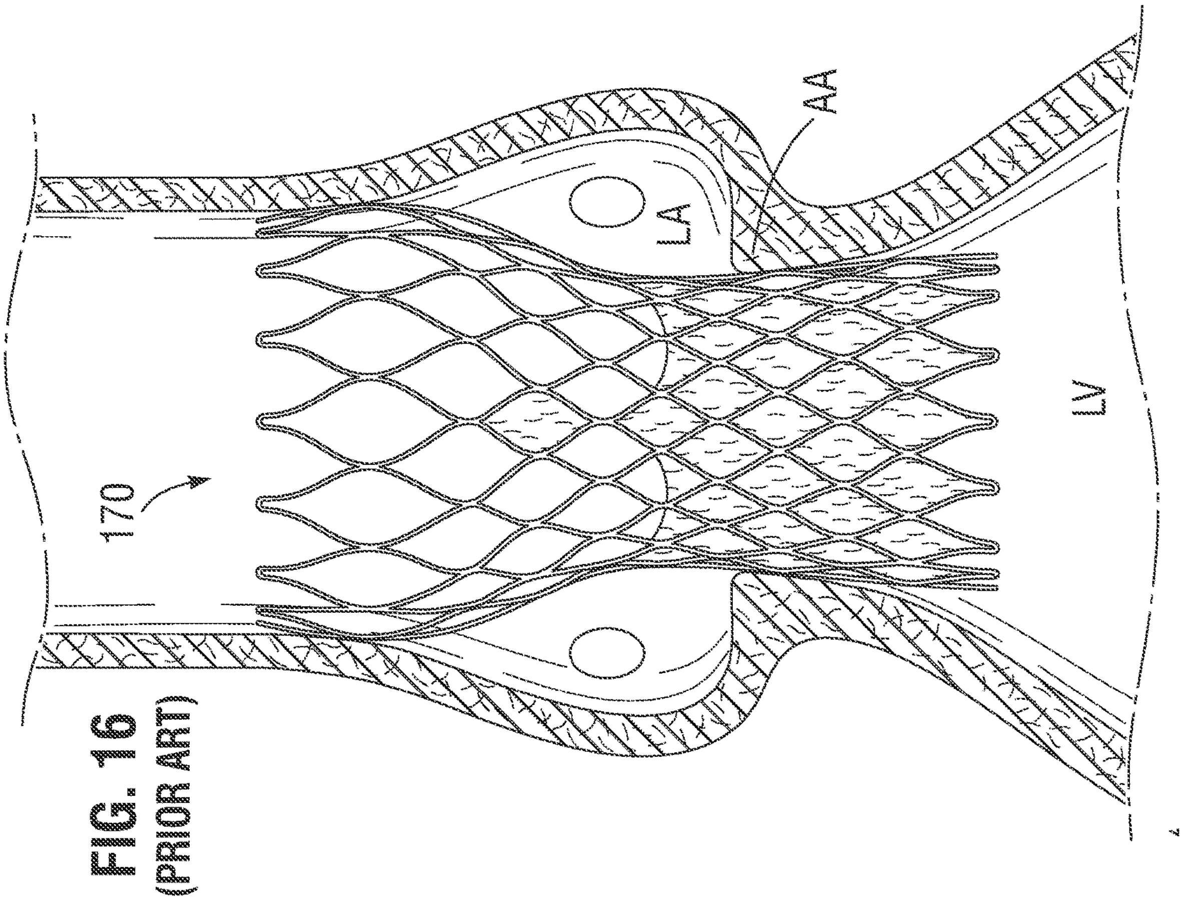
FIG. 16 (PRIOR ART)
FIG. 16 illustrates placement of the fully-expandable prosthetic heart valve of FIG. 15 at an aortic annulus.

The self-expanding nitinol frame 172 may be crimped down to a small diameter just prior to delivery. As shown in FIG. 16, after implantation of the fully-expandable prosthetic heart valve 170 at an aortic annulus, the upper region 180 enlarges into the ascending aorta, the narrow middle region 182 registers with the aortic annulus AA, and the lower region 184 enlarges into the left ventricle LV, or in a subvalvular area. Although the frame 172 is self-expandable and thus exerts less outward force on the surrounding tissue, issues may arise from contact with the adjacent conduction system of the heart, especially in the subvalvular area. Moreover, many surgeons perform a post-implant balloon expansion of the middle region 182 to help fully expand the frame 172, which may also negatively impact the conduction system.

Figure 17B:
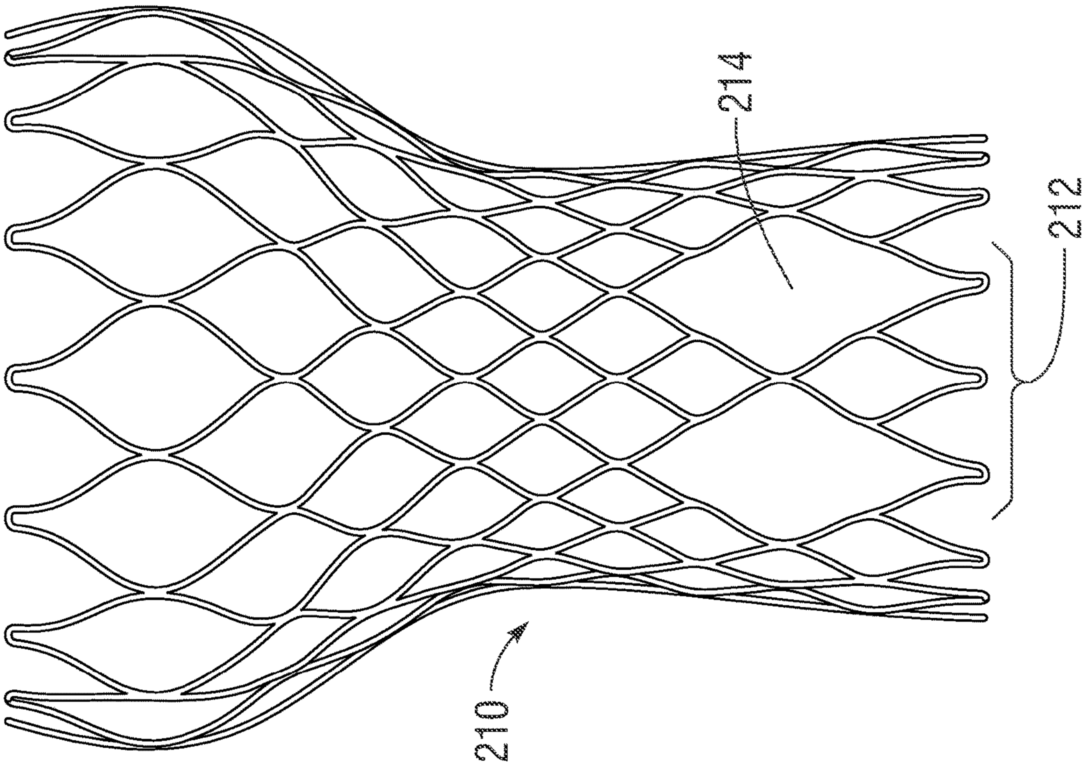
FIGS. 17A and 17B are elevational views of fully-expandable prosthetic heart valves like that shown in FIG. 15 with a portion modified to reduce impact on an adjacent heart conduction system.
Figure 17A:
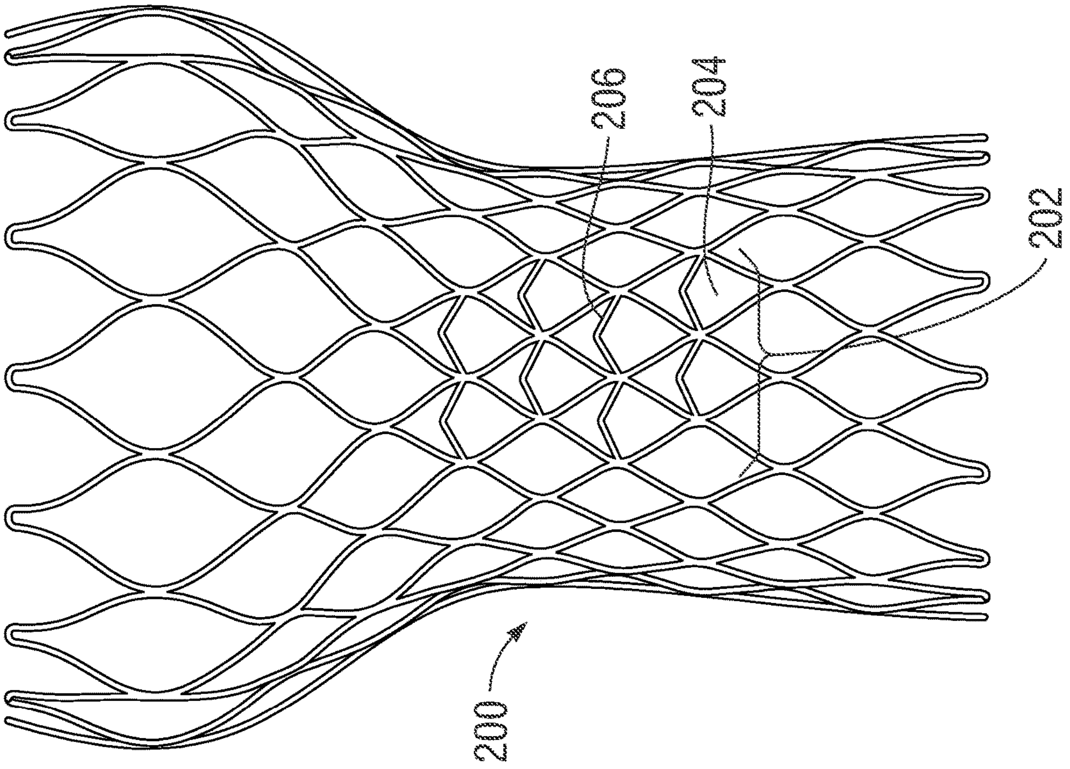

Consequently, FIGS. 17A and 17B show self-expandable stent frames for fully-expandable prosthetic heart valves like that shown in FIG. 15 with a portion modified to reduce impact on an adjacent heart conduction system. In particular, the stent frame 200 in FIG. 17A features a region 202 (bracketed) with modified struts which cause asymmetric expansion of the frame; namely, less expansion within the region 202 as compared to the rest of the circumference. There are a number of ways to modify the struts to accomplish this, one of which includes smaller cells 204 between struts connected by short V-shaped segments 206. The struts 206 that form the smaller cells 204 expand somewhat, but not as much as the surrounding struts. If the valve in which the stent frame 200 is used is for aortic valve replacement, the region 202 is preferably centered on one of the valve commissures, and may extend circumferentially around the valve by between 90-120°. Additionally, the modified region 202 is preferably located in the subvalvular area, preferably in the lower region 184 as see in FIG. 15, but also possibly extending up into the middle region 182.

FIG. 17B, on the other hand, illustrates a self-expandable stent frame 210 with a region 212 (bracketed) modified to reduce the impact on an adjacent conduction system by removing a number of struts to form enlarged cells 214. In the illustrated embodiment, two enlarged diamond-shaped cells 214 are formed by removing four intersecting struts in two places, though other patterns are also contemplated. Removal of the struts lessens the chance that the expanding frame 210 will contact and negatively impact the adjacent conduction system. Again, for aortic valve replacement, the region 212 is preferably centered on one of the valve commissures, and may extend circumferentially around the valve by between 90-120°, and is preferably located in the subvalvular area. A combination of enlarged cells as at 214 and asymmetric expansion as with stent 200 of FIG. 17A is also a possibility.

Modified Expansion Balloons

Figure 18:
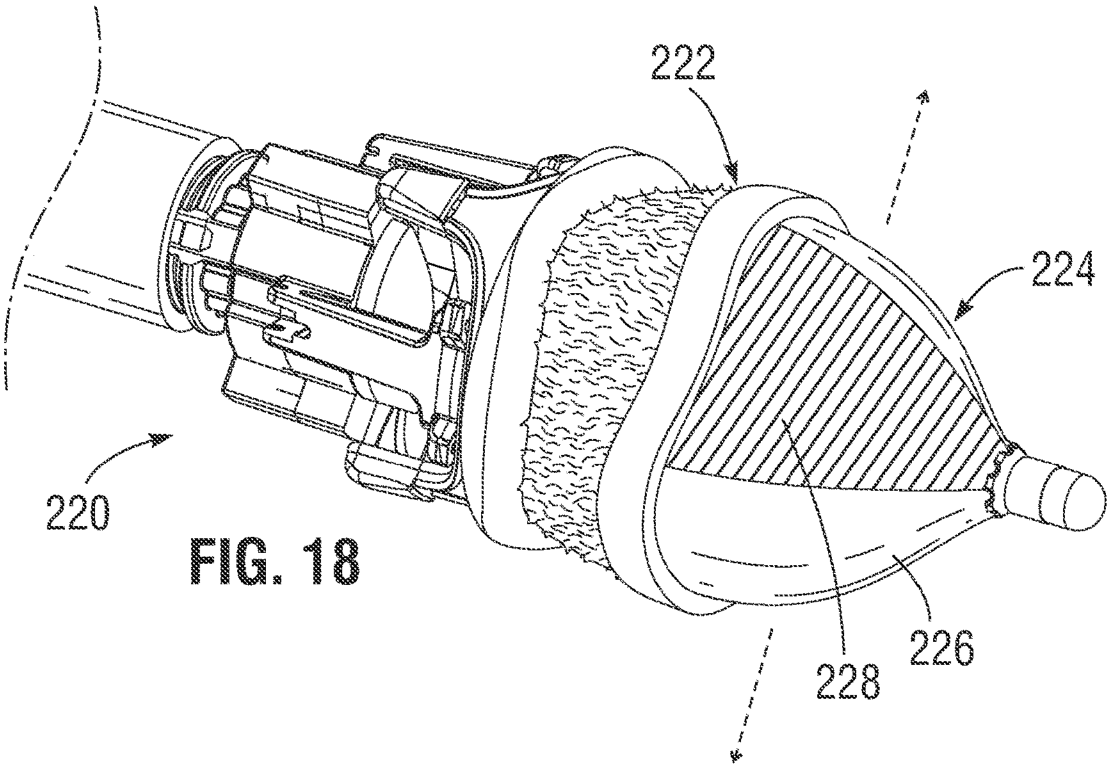
FIG. 18 is a perspective view of a hybrid prosthetic heart valve/holder combination on a distal end of a valve delivery system showing expansion of a distal skirt using an asymmetric balloon.

FIG. 18 is a perspective view of a valve delivery system 220 similar to that described above with respect to FIG. 1 having a hybrid prosthetic heart valve 222 on a distal end thereof. As before, expansion of a distal skirt of the heart valve 222 is accomplished using a balloon 224 that extends through the middle of the valve 222. In contrast with the prior system, the balloon 224 is modified to expand asymmetrically, with a majority of the circumference at 226 being conventional and an altered region 228. Specifically, the region 228 is altered so as to expand less than the larger region 226. Consequently, the portion of the skirt of the heart valve 222 adjacent the modified region 228 expands less as well.

The region 228 may be modified in a number of ways to undergo a smaller radial expansion. One way is to construct the balloon 224 to have the larger region formed of compliant (e.g., stretchy) balloon material with the region 228 formed of non-compliant (e.g., non-stretchy) material. Various balloons of both types of material are known, typically formed out of nylon, e.g., polyether block-amide (e.g., PEBAX®, Arkema) blend or nylon/polyether-block-amide blend materials. In one embodiment, a mesh of interconnected fibers (not shown) may be embedded within the region 228 of an otherwise homogenous balloon to create the non-compliant section. Alternatively, rigid stiffeners (also not shown) such as nylon cords may be attached to the balloon 224 in the region 228. In any event, the region 228 is modified to create an asymmetric expansion of the balloon 224, which in turn expands the valve skirt asymmetrically.

Moreover, the balloon 224 may be combined with a modified hybrid valve as discussed above, and the region 228 aligned to expand within the region of the stent frame that is modified. For instance, the region 228 may extend circumferentially between 90-120°, and be aligned within the region 120*a* of the stent frame 52*a* in FIG. 9A (or within any of the other modified stent frames). Although the various modified stent frames are intended to expand asymmetrically, the modified regions may simply pull the remainder of the frames toward that region, resulting in less asymmetry as desired. Consequently, using a modified expansion balloon 224 may be needed to result in the desired asymmetry.

Figure 19:
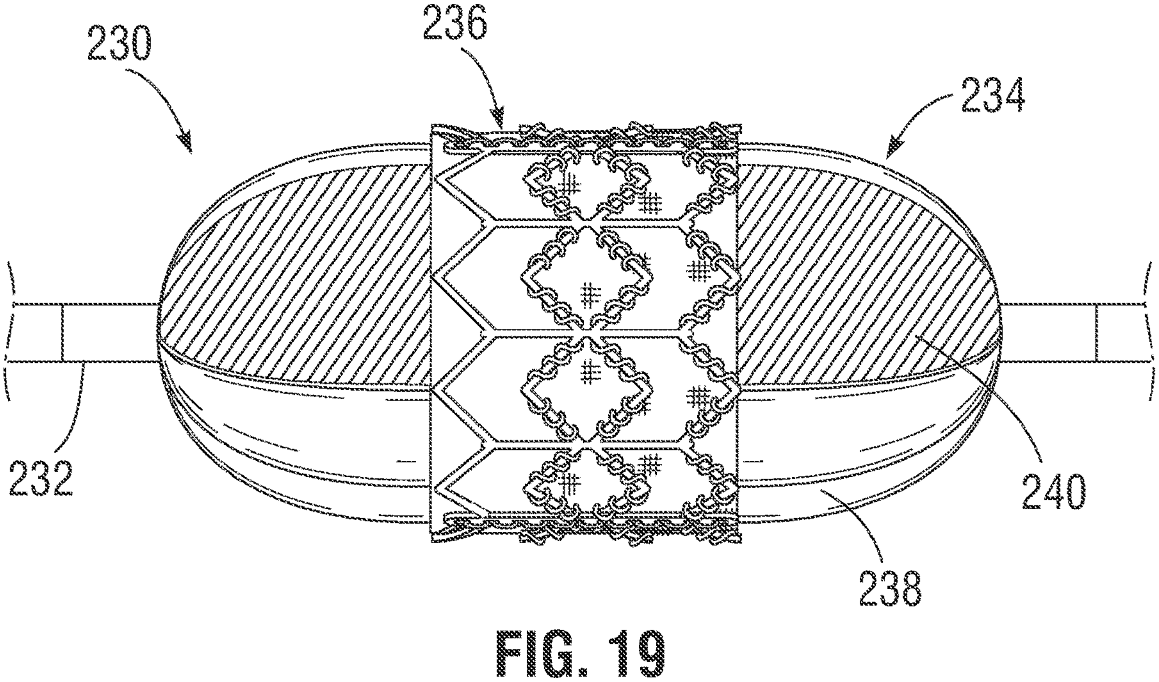
FIG. 19 is a perspective view of a fully-expandable prosthetic heart valve on a distal end of a valve delivery tube showing expansion thereof using an asymmetric balloon.

FIG. 19 is a perspective view of the distal end of a valve delivery system 230 including a catheter 232 and an asymmetric balloon 234 within a fully-expandable prosthetic heart valve 236. The balloon 234 preferably has a majority region 238 that expands normally and a modified region 240 that expands asymmetrically. The modified region 240 may be formed as described above for balloon 224, such as being formed of a non-compliant material. When expanded within the heart valve 236, the asymmetric expansion causes similar asymmetric expansion of the valve. Further, the asymmetric balloon 234 may be used within a fully-expandable prosthetic heart valve 160 modified as described above with respect to FIG. 14. In such a combination, the modified region 240 is rotationally aligned within the region 162 on the valve 160 modified for reduced expansion.

Figure 20A:
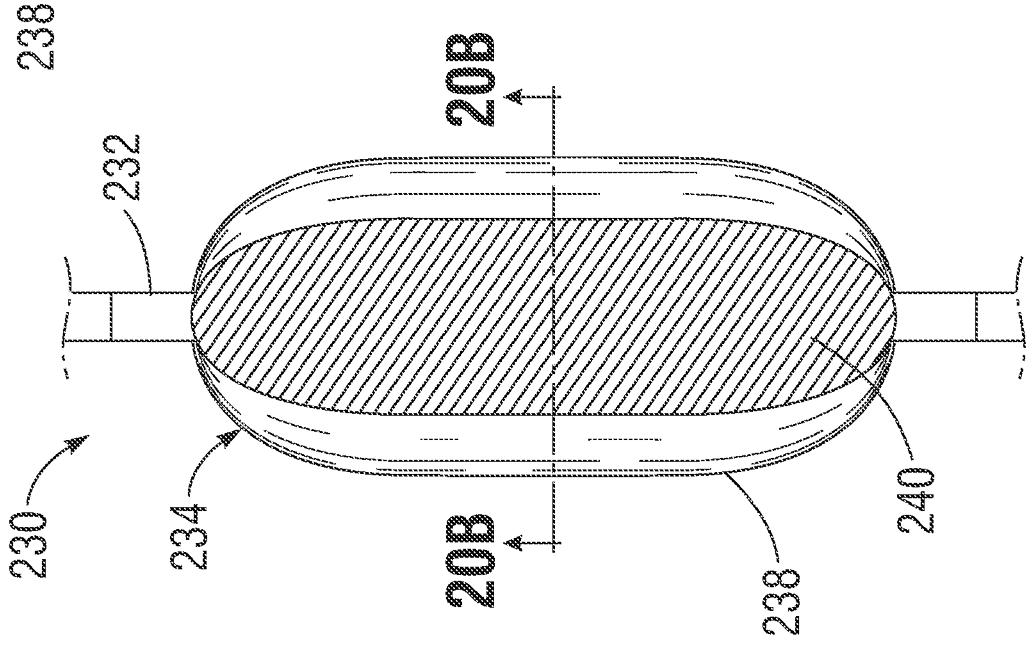
FIG. 20A is an elevational view of an asymmetric balloon used to expand heart valves as modified herein.
Figure 20B:
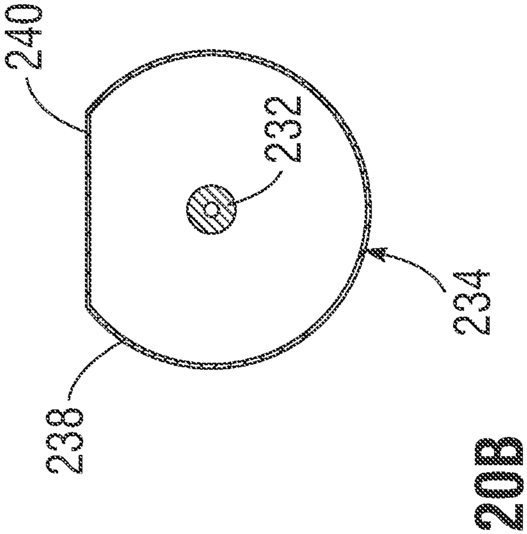
FIG. 20B is a cross-sectional view taken along line 20B-20B in FIG. 20A.

FIG. 20A is an elevational view of the valve delivery system 230 having the asymmetric balloon 234, and FIG. 20B is a cross-sectional view taken along line 20B-20B in FIG. 20A. As mentioned, the modified region 240 is non-compliant or stiffened so as to expand asymmetrically, as seen in FIG. 20B.

Figure 21:
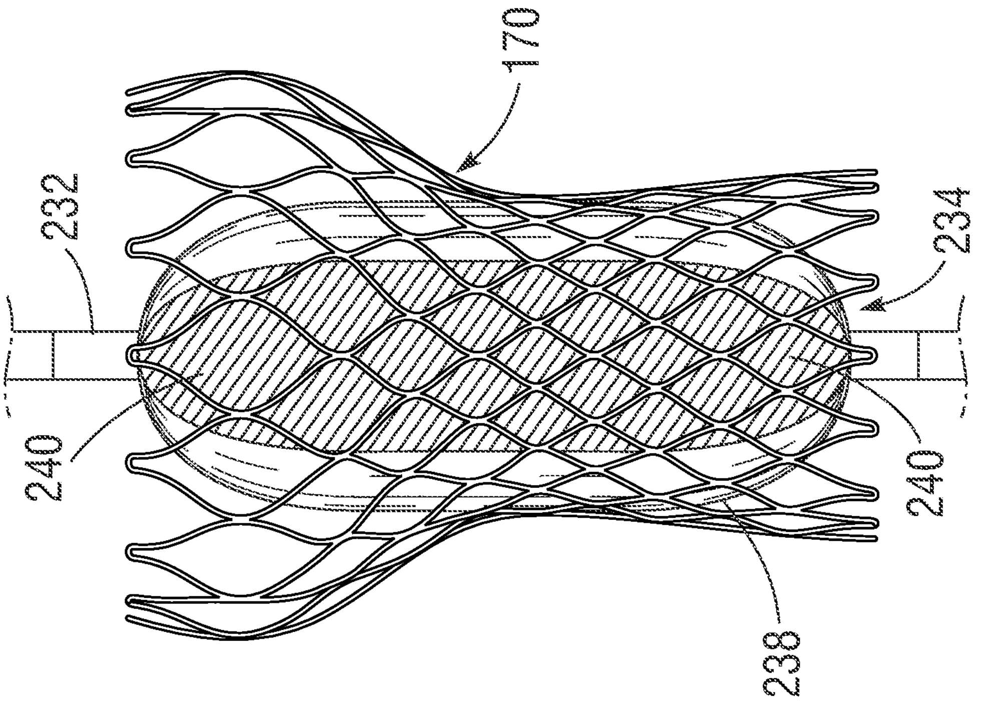
FIG. 21 is an alternative asymmetric balloon used to expand heart valves as modified herein.

FIG. 21 shows the asymmetric balloon 234 within the self-expandable prosthetic heart valve 170 of the prior art during a procedure of post-implant expansion thereof. Preferably, the modified region 240 is rotationally aligned with the area adjacent the valve annulus containing the electrical conduction system of the heart. The asymmetric balloon 234 thus avoids maximum expansion of the frame of the valve 170 in this area. Further, the valve 170 may be modified to reduce the impacts on the conduction system, as with valves 200 and 210 of FIGS. 17A and 17B. In that case, the modified region 240 is rotationally aligned with the modified regions 202, 212, respectively.

While this disclosure describes preferred embodiments, it is to be understood that the words which have been used are words of description and not of limitation. Therefore, changes may be made within the appended claims without departing from the true scope of the disclosure.

What is claimed is:

1. A prosthetic heart valve configured for implant at an aortic annulus, comprising:

a valve member having a non-expandable, non-collapsible annular support frame surrounding and supporting three flexible leaflets arranged to close together along a flow axis through the valve member to prevent blood flow in one direction, the support frame defining three commissure posts at intersections between the leaflets, the valve member and its components having an inflow end and an outflow end with blood permitted to flow through the heart valve in an outflow direction;

a plastically-expandable stent connected to and extending axially away from the inflow end of the support frame such that an outflow end of the stent end is generally annular and non-expandable and non-collapsible at the connection as a consequence, the stent having an inflow end spaced axially from the inflow end of the support frame that is convertible from a radially contracted configuration to a radially expanded configuration, the stent being defined by a plurality of interconnected struts, wherein a pattern of the interconnected struts at the inflow end is consistent around a circumference of the stent except in a modified region on one circumferential side in alignment with one of the three commissure posts so that when converted to the expanded configuration the modified region has larger cells defined between the interconnected struts than around a remainder of the circumference and the modified region expands radially outward a smaller distance than outside of the modified region; and a sealing ring circumscribing the valve at an axial location approximately at the connection between the valve member and the stent, the sealing ring being formed of suture-permeable material and presents an outward flange sized to contact an outflow side of the aortic annulus when implanted.

2. The heart valve of claim 1, wherein the plurality of interconnected struts includes a series of circumferential rows of row struts between axial columns of column struts, the row struts defining bends between the column struts, and wherein the row struts in the modified region of at least one row define shallower bends than the row struts outside of the modified region so that when converted to the expanded configuration the row struts in the modified region of the at least one row define final bend angles.

3. The heart valve of claim 2, wherein final bend angles of the row struts in the modified region of the at least one row are between about 135-160°, while final bend angles of the row struts of the at least one row outside of the modified region are between about 45-90°.

4. The heart valve of claim 2, wherein there are different final bend angles of the row struts in the modified region of the at least one row.

5. The heart valve of claim 1, wherein the plurality of interconnected struts includes a series of circumferential rows of row struts between axial columns of column struts, the row struts defining bends between the column struts, and wherein the larger cells are defined by at least one missing row strut in at least one row in the modified region.

6. The heart valve of claim 1, wherein the plurality of interconnected struts includes a series of circumferential rows of row struts between axial columns of column struts, the row struts defining bends between the column struts, and wherein the larger cells are defined by at least one missing row strut in the modified region in at least one row and at least one missing axial column strut in the modified region in at least one column.

7. The heart valve of claim 1, wherein the modified region extends circumferentially between about 90-120°.

8. The heart valve of claim 1, wherein the modified region extends circumferentially about 120°.

9. The heart valve of claim 1, wherein the modified region is centered in alignment with the one of the three commissure posts.

10. The heart valve of claim 1, wherein the sealing ring has a distinct elongated marking thereon aligned with the modified region of the stent.

11. The heart valve of claim 10, wherein the elongated marking extends circumferentially about 120° and extends between two cusp markings on the sealing ring.

12. A prosthetic heart valve configured for implant at an aortic annulus, comprising:

a valve member having a non-expandable, non-collapsible annular support frame surrounding and supporting three flexible leaflets arranged to close together along a flow axis through the valve member to prevent blood flow in one direction, the support frame defining three commissure posts at intersections between the leaflets, the valve member and its components having an inflow end and an outflow end with blood permitted to flow through the heart valve in an outflow direction; and a plastically-expandable stent connected to and extending axially away from the inflow end of the support frame such that an outflow end of the stent is generally annular and non-expandable and non-collapsible at the connection as a consequence, the stent having an inflow end spaced axially from the inflow end of the support frame that is convertible from a radially contracted configuration to a radially expanded configuration, the stent being evenly expandable around a circumference of the stent except in a modified region on one circumferential side in alignment with one of the three commissure posts so that when converted to the expanded configuration the modified region expands radially outward a smaller distance than outside of the modified region; and a sealing ring circumscribing the valve at an axial location approximately at the connection between the valve member and the stent, the sealing ring being formed of suture-permeable material and presents an outward flange sized to contact an outflow side of the aortic annulus when implanted, wherein the sealing ring has a distinct elongated marking thereon aligned with the modified region of the stent.

13. The heart valve of claim 12, wherein the elongated marking extends circumferentially about 120° and extends between two cusp markings on the sealing ring.

14. The heart valve of claim 12, wherein the stent is defined by a plurality of interconnected struts and a pattern of the interconnected struts at the inflow end is consistent around a circumference of the stent except in the modified region so that when converted to the expanded configuration the modified region has larger cells defined between the interconnected struts than around a remainder of the circumference.

15. The heart valve of claim 14, wherein the plurality of interconnected struts includes a series of circumferential rows of row struts between axial columns of column struts, the row struts defining bends between the column struts, and wherein the row struts in the modified region of at least one row define shallower bends than the row struts outside of the modified region so that when converted to the expanded configuration the row struts in the modified region of the at least one row define final bend angles.

16. The heart valve of claim 15, wherein final bend angles of the row struts in the modified region of the at least one row are between about 135-160°, while final bend angles of the row struts of the at least one row outside of the modified region are between about 45-90°.

17. The heart valve of claim 15, wherein there are different final bend angles of the row struts in the modified region of the at least one row.

18. The heart valve of claim 14, wherein the plurality of interconnected struts includes a series of circumferential rows of row struts between axial columns of column struts, the row struts defining bends between the column struts, and wherein the larger cells are defined by at least one missing row strut in at least one row in the modified region.

19. The heart valve of claim 14, wherein the plurality of interconnected struts includes a series of circumferential rows of row struts between axial columns of column struts, the row struts defining bends between the column struts, and wherein the larger cells are defined by at least one missing row strut in the modified region in at least one row and at least one missing axial column strut in the modified region in at least one column.

20. The heart valve of claim 12, wherein the modified region extends circumferentially between about 90-120°.

21. The heart valve of claim 12, wherein the modified region extends circumferentially about 120°.

22. The heart valve of claim 12, wherein the modified region is centered in alignment with the one of the three commissure posts.

* * * * *